(12) United States Patent
Huang et al.

(10) Patent No.: US 10,066,221 B1
(45) Date of Patent: Sep. 4, 2018

(54) METHODS FOR SCREENING AND USING CRISPR/CAS9 GUIDANCE RNA SEQUENCE FROM HIV PROVIRUS GENOME

(71) Applicants: Zaohua Huang, Palmetto Bay, FL (US); Madhavan Nair, Coral Gables, FL (US)

(72) Inventors: Zaohua Huang, Palmetto Bay, FL (US); Madhavan Nair, Coral Gables, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/449,181

(22) Filed: Mar. 3, 2017

(51) Int. Cl.
 C12N 9/22 (2006.01)
 C12N 15/90 (2006.01)
 A61K 38/00 (2006.01)

(52) U.S. Cl.
 CPC .............. *C12N 9/22* (2013.01); *C12N 15/907* (2013.01); *A61K 38/00* (2013.01)

(58) Field of Classification Search
 None
 See application file for complete search history.

(56) References Cited

PUBLICATIONS

Peng et al., Scientific Reports vol. 3 (2013) pp. 1218-1231.*
Anders C., et al., "Structural Basis of PAM-Dependent Target DNA Recognition by the Cas9 Endonuclease," *Nature*, Jul. 2014, 513(7519):569-73 doi: 10.1038/nature13579.
Bagasra, O. et al. "Cellular Reservoirs of HIV-1 in the Central Nervous System of Infected Individuals: Identification by the Combination of in Situ Polymerase Chain Reaction and Immunohistochemistry." *AIDS*, Abstract.
Barboric, M et al., "NF-kappaB Binds P-Tefb to Stimulate Transcriptional Elongation by RNA Polymerase II," *Molecular Cell*, Aug. 2001, 8(2):327-37, doi: 10.1016/S1097-2765(01)00314-8.
Brady, T. et al., "HIV Integration Site Distributions in Resting and Activated CD4+ T Cells Infected in Culture." *AIDS*, Jul. 2009, 23(12):1461-71, doi: 10.1097/QAD.0b013e32832caf28.
Chavez, L. et al., "HIV Latency is Established Directly and Early in Both Resting and Activated Primary CD4 T Cells," *PLoS Pathogens*, Jun. 2015, 11(6):e1004955, doi: 10.1371/journal.ppat.1004955.
Chen, S. et al., "Genome-Wide CRISPR Screen in a Mouse Model of Tumor Growth and Metastasis." *Cell*, Mar. 2015, 160(6):1246-60, doi: 10.1016/j.cell.2015.02.038.
Chun, T.W. et al., "Early Establishment of a Pool of Latently Infected, Resting CD4(+) T Cells During Primary HIV-1 Infection." *Proceedings of the National Academy of Sciences of the United States of America*, Jul. 1998, 95(15):8869-73.

Chun, T.W. et al., "Induction of HIV-1 Replication in Latently Infected CD4+ T Cells Using a Combination of Cytokines" *The Journal of Experimental Medicine*, Jul. 1998, 188(1):83-91.
Chun, T.W. et al.,"Persistence of HIV in Gut-Associated Lymphoid Tissue Despite Long-Term Antiretroviral Therapy." *The Journal of Infectious Diseases*, Feb. 2008, 197(5):714-20, doi: 10.1086/527324.
Chun, T.W. et al., "Presence of an Inducible HIV-1 Latent Reservoir During Highly Active Antiretroviral Therapy." *Proceedings of the National Academy of Sciences of the United States of America*, Nov. 1997, 94(24):13193-7.
Chun, T.W. et al., "Quantification of Latent Tissue Reservoirs and Total Body Viral Load in HIV-1 Infection." *Nature*, Jun. 1997, 387(6629):183-8, doi: 10.1038/387183a0.
Churchill, M.J. et al., "Extensive Astrocyte Infection is Prominent in Human Immunodeficiency Virus-Associated Dementia." *Annals of Eurology*, Aug. 2009, Abstract.
Churchill, M.J. et al., "Use of Laser Capture Microdissection to Detect Integrated HIV-1 DNA in Macrophages and Astrocytes from Autopsy Brain Tissues." *Journal of Neurovirology*, Mar. 2006, Abstract.
Cong, L. et al., "Multiplex Genome Engineering Using CRISPR/Cas Systems." *Science*, Feb. 2013, 339(6121):819-23, doi: 10.1126/science.1231143.
Dahabieh, M.S. et al., "A Doubly Fluorescent HIV-1 Reporter Shows that the Majority of Integrated HIV-1 is Latent Shortly After Infection." *Journal of Virology*, Feb. 2013, 87(8):4716-27, doi: 10.1128/JVI.03478-12.
Dampier, W. et al., "HIV Excision Utilizing CRISPR/Cas9 Technology: Attacking the Proviral Quasispecies in Reservoirs to Achieve a Cure." *MOJ Immunology*, Oct. 2014, 1(4):1-9, doi: 10.15406/moji.2014.01.00022.
De Luca, M.A. et al., "Lactoferrin- and Antitransferrin-Modified Liposomes for Brain Targeting of the NK3 Receptor Agonist Senktide: Preparation and in Vivo Evaluation." *International Journal of Pharmaceutics*, Jan. 2015, 479(1):129-37, doi: 10.1016/j.ijpharm.2014.12.057.
Ding, H. et al., "Enhanced Blood-Brain Barrier Transmigration Using a Novel Transferrin Embedded Fluorescent Magneto-Liposome Nanoformulation." *Nanotechnology*, Feb. 2014, 25(5):055101, doi: 10.1088/0957-4484/25/5/055101.

(Continued)

*Primary Examiner* — James S Ketter
(74) *Attorney, Agent, or Firm* — Saliwanchik, Lloyd & Eisenschenk

(57) ABSTRACT

The invention pertains to compositions and methods for identifying gRNAs that are effective in treating a latent HIV infection. An embodiment of the invention provides a cell having incorporated into its genome: a gene that expresses a CRISPR-Cas protein and an HIV pseudovirus genome, wherein the HIV pseudovirus genome has a first marker gene encoding a first marker protein under the control of HIV-1 LTR promoter and a second marker gene inserted into the nef gene of the HIV pseudovirus and encoding a second marker protein under the control of a constitutive promoter. Screening methods for identifying gRNAs that can treat a latent HIV infection are also provided. Further, compositions comprising a CRISPR-Cas protein and gRNAs that can treat a latent HIV infection are provided. Furthermore, a method for treating a latent HIV infection in a subject by administering the compositions of CRISPR-Cas protein and gRNAs are described.

15 Claims, 11 Drawing Sheets
(10 of 11 Drawing Sheet(s) Filed in Color)
Specification includes a Sequence Listing.

(56) References Cited

PUBLICATIONS

Ebina, H. et at, "Harnessing the CRISPR/Cas9 System to Disrupt Latent HIV-1 Provirus." *Scientific Reports*, Aug. 2013, 3:2510, doi: 10.1038/srep02510.

Finzi, D. et al., "Identification of a Reservoir for HIV-1 in Patients on Highly Active Antiretroviral Therapy." *Science*, Dec. 1997, 278(5341):1295-300, doi: 10.1126/science.278.5341.1295.

Fischer-Smith, T. et al., "CNS Invasion by CD14+/CD16+ Peripheral Blood-Derived Monocytes in HIV Dementia: Perivascular Accumulation and Reservoir of HIV Infection." *Journal of Neurovirology*, Nov. 2001, 7(6):528-41, doi: 10.1080/135502801753248114.

Fletcher, C.V. et al., "Persistent HIV-1 Replication is Associated with Lower Antiretroviral Drug Concentrations in Lymphatic Tissues." *Proceedings of the National Academy of Sciences of the United States of America*, Feb. 2014, 111(6):2307-12, doi: 10.1073/pnas.1318249111.

Gallastegui, E. et al., "Chromatin Reassembly Factors are Involved in Transcriptional Interference Promoting HIV Latency." *Journal of Virology*, Jan. 2011, 85(7):3187-202, doi: 10.1128/JVI.01920-10.

Gilbert, L.A. et al., "Genome-Scale CRISPR-Mediated Control of Gene Repression and Activation." *Cell*, Oct. 2014, 159(3):647-61, doi: 10.1016/j.cell.2014.09.029.

Heaton, R.K. et al., "HIV-Associated Neurocognitive Disorders Before and During the Era of Combination Antiretroviral Therapy: Differences in Rates, Nature, and Predictors." *Journal of Neurovirology*, Feb. 2011, 17(1):3-16, doi: 10.1007/s13365-010-0006-1.

Heaton, R.K. et al., "HIV-Associated Neurocognitive Disorders Persist in the Era of Potent Antiretroviral Therapy: CHARTER Study." *Neurology*, Dec. 2010, 75(23):2087-96, doi: 10.1212/WNL.0b013e318200d727.

Heaton, R.K. et al., "Neurocognitive Change in the Era of HIV Combination Antiretroviral Therapy: The Longitudinal CHARTER Study." *Clinical Infectious Diseases*, Feb. 2015, 60(3):473-80, doi: 10.1093/cid/ciu862.

Horlbeck, M.A. et al., "Compact and Highly Active Next-Generation Libraries for CRISPR-Mediated Gene Repression and Activation." *eLife*, Sep. 2016, 5:e19760, doi: 10.7554/eLife.19760.

Hsu, P.D. et al., "Development and Applications of CRISPR-Cas9 for Genome Engineering." *Cell*, Jun. 2014, 157(6):1262-78, doi: 10.1016/j.cell.2014.05.010.

Huang, J. et al., "Cellular Micrornas Contribute to HIV-1 Latency in Resting Primary CD4+ T Lymphocytes." *Nature Medicine*, Nov. 2007, 13(10):1241-7, doi: 10.1038/nm1639.

Hu, W. et al., "RNA-Directed Gene Editing Specifically Eradicates Latent and Prevents New HIV-1 Infection." *Proceedings of the National Academy of Sciences of the United States of America*, Jun. 2014, 111(31):11461-6, doi: 10.1073/pnas.1405186111.

Jayant, R.D. et al., "Sustained-Release Nanoart Formulation for the Treatment of neuroAIDS." *International Journal of Nanomedicine*, Feb. 2015, 10:1077-93, doi: 10.2147/IJN.S76517.

Kaminski, R. et al., "Excision of HIV-1 DNA by Gene Editing: A Proof-of-Concept in Vivo Study." *Gene Therapy*, May 2016, Abstract.

Kaminski, R. et al., "Elimination of HIV-1 Genomes from Human T-lymphoid Cells by CRISPR/Cas9 Gene Editing." *Scientific Reports*, Mar. 2016, 6:22555, doi: 10.1038/srep22555.

Kaushik, A. et al., "Magnetically Guided Central Nervous System Delivery and Toxicity Evaluation of Magneto-Electric Nanocarriers." *Scientific Reports*, May 2016, 6:25309, doi: 10.1038/srep25309.

Konermann, S. et al., "Genome-Scale Transcriptional Activation by an Engineered CRISPR-Cas9 Complex." *Nature*, Jan. 2015, 517(7536):583-8, doi: 10.1038/nature14136.

Lenasi, T. et al., "Transcriptional Interference Antagonizes Proviral Gene Expression to Promote HIV Latency." *Cell Host & Microbe*, Aug. 2008, 4(2):123-33, doi: 10.1016/j.chom.2008.05.016.

Letendre, S. et al., "Validation of the CNS Penetration-Effectiveness Rank for Quantifying Antiretroviral Penetration Into the Central Nervous System." *Archives of Neurology*, Jan. 2008, 65(1):65, doi: 10.1001/archneurol.2007.31.

Li, W. et al., "MAGeCK Enables Robust Identification of Essential Genes from Genome-Scale CRISPR/Cas9 Knockout Screens." *Genome Biology*, Dec. 2014, 15(12):554, doi: 10.1186/PREACCEPT-1316450832143458.

McElrath, M.J. et al., "Latent HIV-1 Infection in Enriched Populations of Blood Monocytes and T Cells from Seropositive Patients." *The Journal of Clinical Investigation*, Jan. 1991, 87(1):27-30, doi: 10.1172/JCI114981.

Nair, M. et al., "Externally Controlled On-Demand Release of Anti-HIV Drug Using Magneto-Electric Nanoparticles as Carriers." *Nature Communications*, Apr. 2013, 4:1707, doi: 10.1038/ncomms2717.

Narasipura, S.D. et al., "Epigenetic Regulation of HIV-1 Latency in Astrocytes." *Journal of Virology*, Mar. 2014, 88(5):3031-8, doi: 10.1128/JVI.03333-13.

Nath, A., "Eradication of Human Immunodeficiency Virus from Brain Reservoirs." *Journal of Neurovirology*, Jun. 2015, 21(3):227-34, doi: 10.1007/s13365-014-0291-1.

Nishimasu, H. et al., "Crystal Structure of Cas9 in Complex With Guide RNA and Target DNA." *Cell*, Feb. 2014, 156(5):935-49, doi: 10.1016/j.cell.2014.02.001.

Patel, P. et al., "The Microrna Mir-29a is Associated with Human Immunodeficiency Virus Latency." *Retrovirology*, Dec. 2014, 11:108, doi: 10.1186/PREACCEPT-2650748421390399.

Petito, C.K. et al., "HIV Infection of Choroid Plexus in AIDS and Asymptomatic HIV-Infected Patients Suggests that the Choroid Plexus May Be a Reservoir of Productive Infection." *Journal of Neurovirology*, Jun. 1999, 5(6):670-7.

Qi, L.S. et al., "Repurposing CRISPR as an RNA-Guided Platform for Sequence-Specific Control of Gene Expression." *Cell*, Feb. 2013, 152(5):1173-83, doi: 10.1016/j.cell.2013.02.022.

Ruelas, D.S. et al., "MicroRNA-155 Reinforces HIV Latency." *The Journal of Biological Chemistry*, Apr. 2015, 290(22):13736-48, doi: 10.1074/jbc.M115.641837.

Sagar, V. et al., "Therapeutical Neurotargeting via Magnetic Nanocarrier: Implications to Opiate-Induced Neuropathogenesis and NeuroAIDS." *Journal of Biomedical Nanotechnology*, Oct. 2015, 11(10):1722-33, doi: 10.1166/jbn.2015.2108.

Schneider, M. et al., "A New Model for Post-Integration Latency in Macroglial Cells to Study HIV-1 Reservoirs of The Brain." *AIDS*, Mar. 2015, 29(10):1147-59, doi: 10.1097/QAD.0000000000000691.

Shalem, O. et al., "Genome-Scale CRISPR-Cas9 Knockout Screening in Human Cells." *Science*, Dec. 2013, 343(6166):84-7, doi: 10.1126/science.1247005.

Siliciano, J.D. et al., "Long-Term Follow-Up Studies Confirm the Stability of the Latent Reservoir for HIV-1 in Resting CD4+ T Cells." *Nature Medicine*, Jun. 2003, 9(6):727-8, doi: 10.1038/nm880.

Smith, P.D. et al., "Macrophage HIV-1 Infection and the Gastrointestinal Tract Reservoir." *Journal of Leukocyte Biology*, Nov. 2003, 74(5):642-9, doi: 10.1189/jlb.0503219.

Solas, C. et al. "Discrepancies Between Protease Inhibitor Concentrations and Viral Load in Reservoirs and Sanctuary Sites in Human Immunodeficiency Virus-Infected Patients." *Antimicrobial Agents and Chemotherapy*, Jan. 2003, 47(1):238-43, doi: 10.1128/AAC.47.1.238-243.2003.

Sunshine, S. et al., "HIV Integration Site Analysis of Cellular Models of HIV Latency with a Probe-Enriched Next-Generation Sequencing Assay." *Journal of Virology*, May 2016, 90(9):4511-9, doi: 10.1128/JVI.01617-15.

Wang, T., "Genetic Screens in Human Cells Using the CRISPR-Cas9 System." *Science*, Dec. 2013, 343(6166):80-4, doi: 10.1126/science.1246981.

Wang, T. et al., "Identification and Characterization of Essential Genes in the Human Genome." Science, Nov. 2015, 350(6264):1096-101, doi: 10.1126/science.aac7557.

Zhu, W. et al., "The CRISPR/Cas9 System Inactivates Latent HIV-1 Proviral DNA." *Retrovirology*, Feb. 2015, 12:22, doi: 10.1186/s12977-015-0150-z.

\* cited by examiner

METHODS FOR SCREENING AND USING CRISPR/CAS9 GUIDANCE RNA SEQUENCE FROM HIV PROVIRUS GENOME

GOVERNMENT SUPPORT

This invention was made with government support under DA042706 awarded by the National Institutes of Health. The government has certain rights in the invention.

The Sequence Listing for this application is labeled "SeqList-03Mar17-ST25.txt", which was created on Mar. 3, 2017, and is 4 KB. The entire contents are incorporated herein by reference in its entirety.

BACKGROUND OF THE INVENTION

Human immunodeficiency virus (HIV)/acquired immunodeficiency syndrome (AIDS) is the most severe pandemic disease in modern history and remains a major threat to humans. With HIV/AIDS prevention, diagnosis and treatment, the morbidity and mortality of AIDS decreased significantly. However, AIDS remains an incurable, chronic infection due to the multiple HIV latent cells in a patient.

HIV infection of human cells can be divided into active infection and latent infection. In most human cells, HIV infection is active infection; however, in rare human cells, latent infection can occur at very early stage. These very small numbers of latently infected cells are called HIV reservoirs and they are located mainly in brain, peripheral blood, and lymphoid tissue. The HIV reservoir cells include resting memory T cells in lymph nodes; astrocytes, microglia, and microphages in brain; and resting memory T cells and monocytes in peripheral blood.

To date, the mechanism of the formation of the reservoir and activation of the latent cells remains largely unknown; however, in reservoir cells HIV provirus may be silenced by multiple factors, including integration site, chromatin status, accessibility of transcription factors, and ribonucleic acid (RNA) interference. In the reservoir cell sites antiviral drugs penetration is often low. Moreover, even under antiretroviral therapy (ART), about 30 to 50% of AIDS patients eventually develop HIV-associated neurological disorders (HAND), which are cognitive, motor and/or behavioral impairments caused by HIV infection in human brain. HAND can further be grouped into asymptomatic neurocognitive impairment (ANI), minor neurocognitive disorder (MND) and the most severe HIV-associated dementia (HAD).

The mechanism of HAND remains to be elucidated; however, HAND is tightly correlated with HIV infection of astrocytes, microglia and macrophages in human brains. Neurons are believed to be resistant to HIV infection. However, the neurotoxic products released from HIV infected brain cells seriously dysregulates neuronal function and homeostasis.

Astrocytes are very important supporting cells in human central nervous system and they play critical roles in physiological and pathological conditions. Their functions include being a critical component of Blood Brain Barrier, forming tripartite synapses; being structural scaffold, releasing and up taking neurotransmitters and providing energy substrates to neurons. Moreover, in some pathological conditions, astrocytes' ability to maintain homeostasis is disrupted. HIV and HIV proteins impair astrocytes' ability to maintain homeostasis.

RNA-guided clustered regularly interspaced short palindromic repeat (CRISPR)/CRISPR-associated protein 9 (Cas9) system is derived from the adaptive immune system from bacteria. Cas9 can be bioengineered for better nucleus localization and mammalian cell expression. The original two RNA (crRNA and tracRNA) can be converted into a single guided RNA (gRNA). Cas9 has two nuclease activity domains named HNH and RuvC. Each of these two domains can cleave a DNA strand directed by a gRNA complementary to the target DNA sequence. The prerequisite to be a target sequence is the presence of a NGG sequence (protospacer adjacent motifs, PAM) downstream the target site and the target sequence is generally 20 nucleotides. In the nucleus, Cas9, gRNA, and target DNA form a complex and HNH and RuvC domains each cleave a DNA strand. The double strand breaks are consequently repaired mainly by two approaches: non-homologous end-joining (NHEJ) when a template is absent or homology directed repair (HDR) when a homogenous repair template is present. NHEJ usually results in insertion or deletion (indel), while HDR results in correct repair as directed by the template.

The ultimate cure for HIV/AIDS would be the removal or disruption of integrated HIV provirus in latently infected cells or the complete elimination of these latent cells. However, gene therapy for HIV/AIDS has progressed very slowly.

BRIEF SUMMARY OF THE INVENTION

The invention provides compositions and methods for identifying gRNAs that are effective in treating a latent HIV infection. An embodiment of the invention provides a cell having incorporated into its genome: a gene that expresses a CRISPR-Cas protein and an HIV pseudovirus genome, wherein the HIV pseudovirus genome has a first marker gene encoding a first marker protein under the control of HIV-1 LTR promoter and a second marker gene encoding a second marker protein under the control of a constitutive promoter. In one embodiment, the second marker gene is inserted into the nef gene of the HIV pseudovirus.

In certain embodiments, the cell is a human cell, particularly, a brain cell selected from astrocytes, microglial cells, and brain microphages; or a peripheral blood cell selected from resting memory T cells and monocytes. In a preferred embodiment, the first marker protein is a green fluorescence protein and the second marker protein is a red fluorescence protein.

Screening methods for identifying gRNAs that can remove or disrupt a provirus from the genome of a cell having a latent HIV infection are also provided. The screening methods comprise the steps of incubating the cells of the invention in the presence of one or more gRNAs from the plurality of gRNAs and identifying gRNAs that disrupt the second gene.

Further embodiments of the invention provide a composition comprising a CRISPR-Cas protein and one or more gRNAs that are effective for removing or disrupting an HIV provirus genome integrated into the genome of a cell. Accordingly, an even further embodiment provides a method for treating, suppressing, or eradicating a latent HIV infection in a subject, the method comprising administering into the cells of the subject that carry the latent HIV infection a composition comprising a CRISPR-Cas protein and one or more gRNAs that are effective for removing or disrupting an HIV provirus genome integrated into the genome of a cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BRIEF DESCRIPTION OF SEQUENCES

Figure 1A:
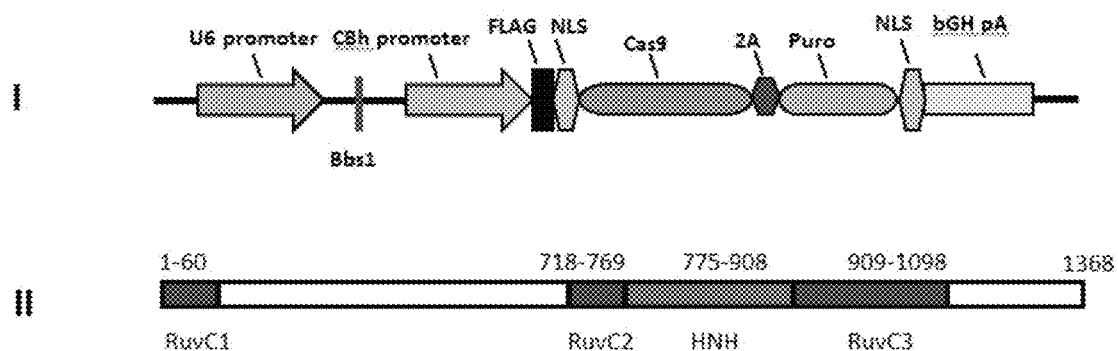
FIGS. 1A-1D. Establishment of stable Cas9 expression astrocyte cell line. 1A. Scheme of humanized Cas9 construct and the protein structure of Cas9. I: Structure of Cas9 vector: major DNA segments of humanized Cas9 construct are presented and their names are listed above the corresponding segment. The digestion site of Bbs1 is also labeled between U6 promoter and CBh promoters. The construct expresses a humanized Cas9 protein with flag tag and NLS domains and confers the transfected cells resistance to puromycin. II: Domain structure of Cas9: Major domains of Cas9 protein are presented and amino acid location of each main domain is also listed above the domain. 1B. Genomic integration of Cas9 construct: Cas9 encoding gene-specific primers were used to screen positive clones that contain the Cas9 construct integration in cell genome. Gapdh PCR products are used as a DNA extracts quality and loading control. Test results of 12 clones were presented. 1C. Cas9 protein expression in isolated cell clones: After cell clone screen by PCR, the protein extracts of 6 positive clones were examined with SDS-PAGE and Western blot to check the protein expression of Cas9. GAPDH protein were also checked and used as a loading control. 1D. Cas9 protein localization: Immunocytochemistry and fluorescence microscopy were used to determine the intracellular localization of Cas9 protein. Nucleus counterstain was used to determine the co-localization of Cas9 and nucleus. The white arrow points to the location of the nucleus.

SEQ ID NO: 1 is a forward primer for Cas amplification.
SEQ ID NO: 2 is a reverse primer for Cas amplification.
SEQ ID NO: 3 is a forward primer for Cas amplification.
SEQ ID NO: 4 is a reverse primer for Cas amplification.
SEQ ID NO: 5 is a forward primer for mCherry amplification.
SEQ ID NO: 6 is a reverse primer for mCherry amplification.
SEQ ID NO: 7: A forward primer for mCherry amplification.
SEQ ID NO: 8 is a reverse primer for mCherry amplification.
SEQ ID NO: 9 is a forward primer for LTR region amplification.
SEQ ID NO: 10 is a reverse primer for LTR region amplification.
SEQ ID NO: 11: A forward primer for LTR region amplification.
SEQ ID NO: 12 is a reverse primer for LTR region amplification.
SEQ ID NO: 13 is a gLTR sequence.
SEQ ID NO: 14 is a gnef sequence.
SEQ ID NO: 15 is a gtat sequence.
SEQ ID NO: 16 is a gpol sequence.
SEQ ID NO: 17 is a forward primer for detecting deletion gnef and gpol.
SEQ ID NO: 18 is a forward primer for detecting deletion of gnef and gtat.

DETAILED DISCLOSURE OF THE INVENTION

The core components of CRISPR/Cas9 system are Cas9 nuclease and gRNA. gRNA determines the specificity of gene-editing. gRNA has two forms: one form consists of two components: crRNA and tracRNA, and the other form merges the two RNAs into one single gRNA, named sgRNA. crRNA and tracRNA can be chemically synthesized and quantitatively applied, while the sgRNA is often applied in the form of a DNA plasmid or in the form of mRNA purified from in vitro transcription.

HIV has a genome of about 10 kb while a gRNA typically targets 20 bp nucleotide sequence. Therefore, thousands of candidate gRNA targeting sequences are available to target the HIV provirus in HIV latent cells. The invention provides a screening method for identifying target gRNA sequences in HIV provirus. The target gRNA sequences can be used in gene therapy for suppressing, treating, or eradicating a latent HIV infection.

Most CRISPR gRNA library screening methods are mainly used for genome-wide knockout, transcription repression, or activation. The gRNA libraries are usually in the form of lentiviral vectors and the gRNAs in the library typically target all the genes in the genome. Each target gene has several gRNAs. After screening, cell clones are expanded and sequenced by next generation sequencing. The gRNA library screening methods are designed to find essential biological functions of specific gene or genes and to identify signal transduction pathways. A screening assay for evaluating gRNA efficiency is not available.

The invention provides a cell line with HIV reporter and stable Cas9 expression. The cell lines of the invention can be used in a screening assay to identify candidate gRNAs and to evaluate efficiency of a gRNA in treating a latent HIV infection.

Accordingly, an embodiment of the invention provides a eukaryotic cell having incorporated into the genome of the cell: a gene that expresses a clustered regularly interspaced short palindromic repeats (CRISPR)-associated (Cas) protein and an HIV pseudovirus genome having a first marker gene encoding a first marker protein under the control of HIV-1 LTR promoter and a second marker gene encoding a second marker protein under the control of a constitutive promoter. In one embodiment, the second marker gene is inserted into the nef gene of the HIV pseudovirus.

An HIV pseudovirus genome is an HIV genome incapable of producing HIV particles and, hence, incapable of propagating and infecting new cells. In one embodiment, the HIV pseudovirus has a defective env gene that does not produce a functional envelope protein and/or a defective nef gene that does not produce a functional nef protein. In a preferred embodiment, the HIV pseudovirus has a defective env gene and a defective nef gene.

The eukaryotic cell can be an animal cell, for example, a mammalian or an insect cell. In specific embodiments, the cell is a brain cell, for example, astrocytes, microglia, and microphages in brain; a peripheral blood cell, for example, resting memory T cells and monocytes; or a lymphoid cell, for example, resting memory T cells.

CRISPR-Cas protein is an RNA-guided endonuclease that catalyzes site-specific cleavage of double stranded DNA. In one embodiment, CRISPR-Cas protein is Cas9/Csn1. A skilled artisan can identify a CRISPR-Cas protein from a given bacterium and use as described herein and such embodiments are within the purview of the invention. In certain embodiments, a CRISPR-Cas protein is genetically modified to have a eukaryotic nuclear localization signal, particularly, a nuclear localization signal that is optimized for the host eukaryotic cell. In another embodiment, the CRISPR-Cas gene is genetically optimized for expression in a host eukaryotic cell, for example, by codon optimization.

Marker proteins useful in the cells described herein include enzymes, antibiotic resistance proteins, and florescent proteins. Examples of marker proteins that are enzymes include horseradish peroxidase, alkaline phosphatase, luciferase, galactosidase, and glucose oxidase. Examples of antibiotic resistance proteins include proteins that confer resistance to antibiotics against mammalian cells, for example, blasticidin, geneticin, hygromycin, mycophenolic acid, puromycin, and zeocin. Examples of marker proteins that are fluorescent proteins include UV proteins, blue proteins, cyan proteins, green proteins, yellow proteins, orange proteins, red proteins, far red proteins, near infra-red proteins, sapphire-type proteins, and long stokes shift proteins. Additional examples of marker proteins useful in the methods described herein are known to a person of ordinary skill in the art and such embodiments are within the purview of the invention.

In a particular embodiment, the first marker protein is a green fluorescence protein and the second marker protein is a red fluorescent protein. In another embodiment, the first marker protein is a red fluorescence protein and the second marker protein is a green fluorescent protein. A skilled artisan can design and prepare a cell containing any combination of a first marker protein and a second marker protein.

A constitutive promoter that drives the expression of a second marker protein is a promoter that constitutively expresses the gene operably linked to the promoter.

Examples of constitutive promoters include SV40, CMV, UBC, EF1A, PGK, and CAG promoters for mammalian cells; COPIA and ACT5C promoters for *drosophila* cells; and Actin 5C or polyhedrin, OpIE2, and P10 promoters for insect cells. Additional examples of constitutive promoters are known in the art and a skilled artisan can identify an appropriate constitutive promoter for a host cell.

In one embodiment, a stable Cas9 astrocyte cell line (FIGS. 1B-1C) is provided. This cell line avoids the need for introducing the Cas9 protein to a screening platform. The stable Cas9 expression makes the cell line fit for gRNAs-focused screening, and the synthetic gRNA approach provided herein facilitate a high-throughput screening.

Stable Cas9 expression in cell lines is long lasting (FIGS. 2B-2D) and does not affect the cell line morphology and other biological parameters.

Figure 2A:
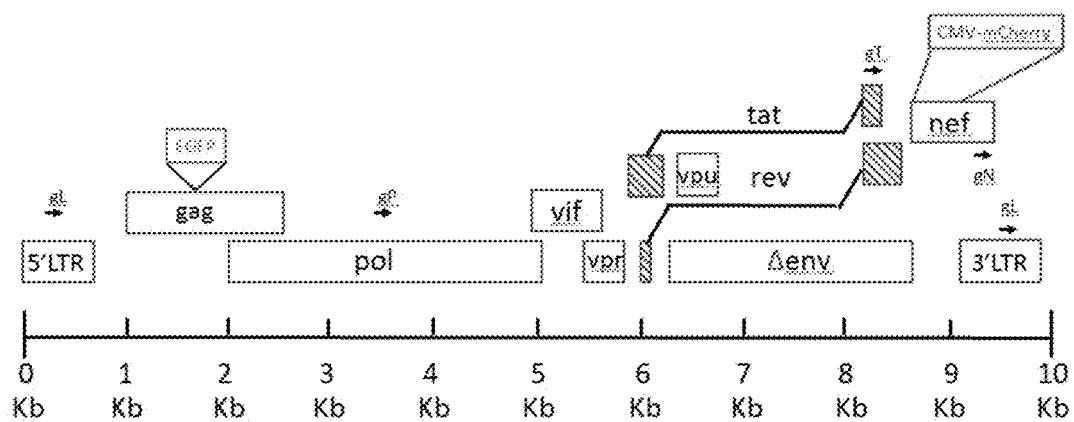
FIGS. 2A-2D. Establishment of HIV latent astrocyte cell model with stable Cas9 expression. A. Scheme of dual fluorescence HIV reporter construct and gRNA target sites: DNA structure of red and green HIV reporter construct are presented and major domain names are listed. 2A nucleotide base pair scale is provided for segment size and order reference. An EGFP expression cassette is inserted into the gag gene and a mCherry expression cassette is inserted into the nef gene. In an embodiment of the HIV pseudovirus genome, both en, gene and nef gene are defective. This construct is not contagious and cannot replicate alone. The gRNA sites are marked with black arrows and the first letter of the region with a g prefix. gL for LTR; gP for pol; gT for tat; gN for nef 2B. Development of latent astrocyte model: The isolated stable Cas9 cell clone in FIG. 1D was infected with HIV reporter pseudotyped with VSVG. In day 2 images, in GFP channel, the green fluorescence protein expression (either alone or with the red fluorescence protein expression, shown by blue arrow) indicates the active state of HIV, while in RFP channel, the red fluorescence only cells were showed by white arrow. In day 10 and 16 images, in RFP channel, the red fluorescence protein only expression (shown by white arrows) indicates the latent status of HIV. 2C. Isolation of latent HIV-Cas9 cell clones: Latent cell clones (2 clones are shown here) which possess the genomic integration of both Cas9 construct and HIV reporter were isolated and expanded. All the cells are expressing red fluorescence protein. 2D. Genomic integration of HIV reporter verification in cell clones: I: HIV provirus confirmation: Multiple HIV reporter specific primers for different regions of constructs were used to verify the selected two positive clones, which have the HIV reporter construct integrated in the cell's genome. Gapdh PCR products are used as a DNA extracts quality and loading control. II: Cas9 protein detection in selected clones: After cell clone confirmation by PCR, the protein extracts of positive clones were examined with SDS-PAGE and Western blot to check the protein expression of Cas9. GAPDH protein were also checked and used as a loading control.
Figure 2B:
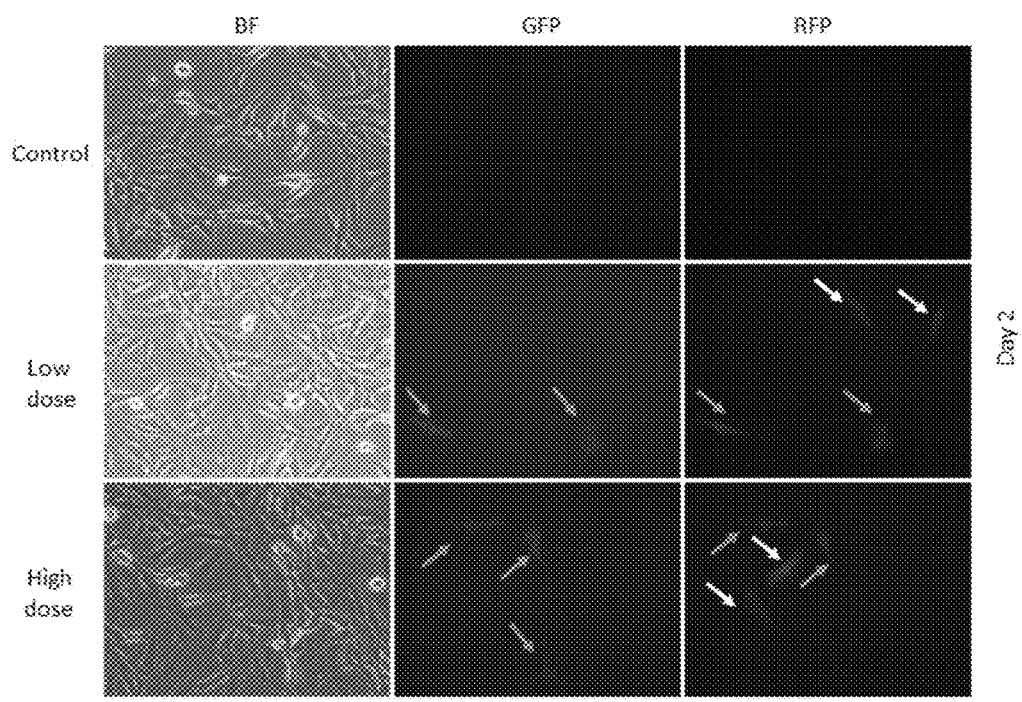
Figure 2B:
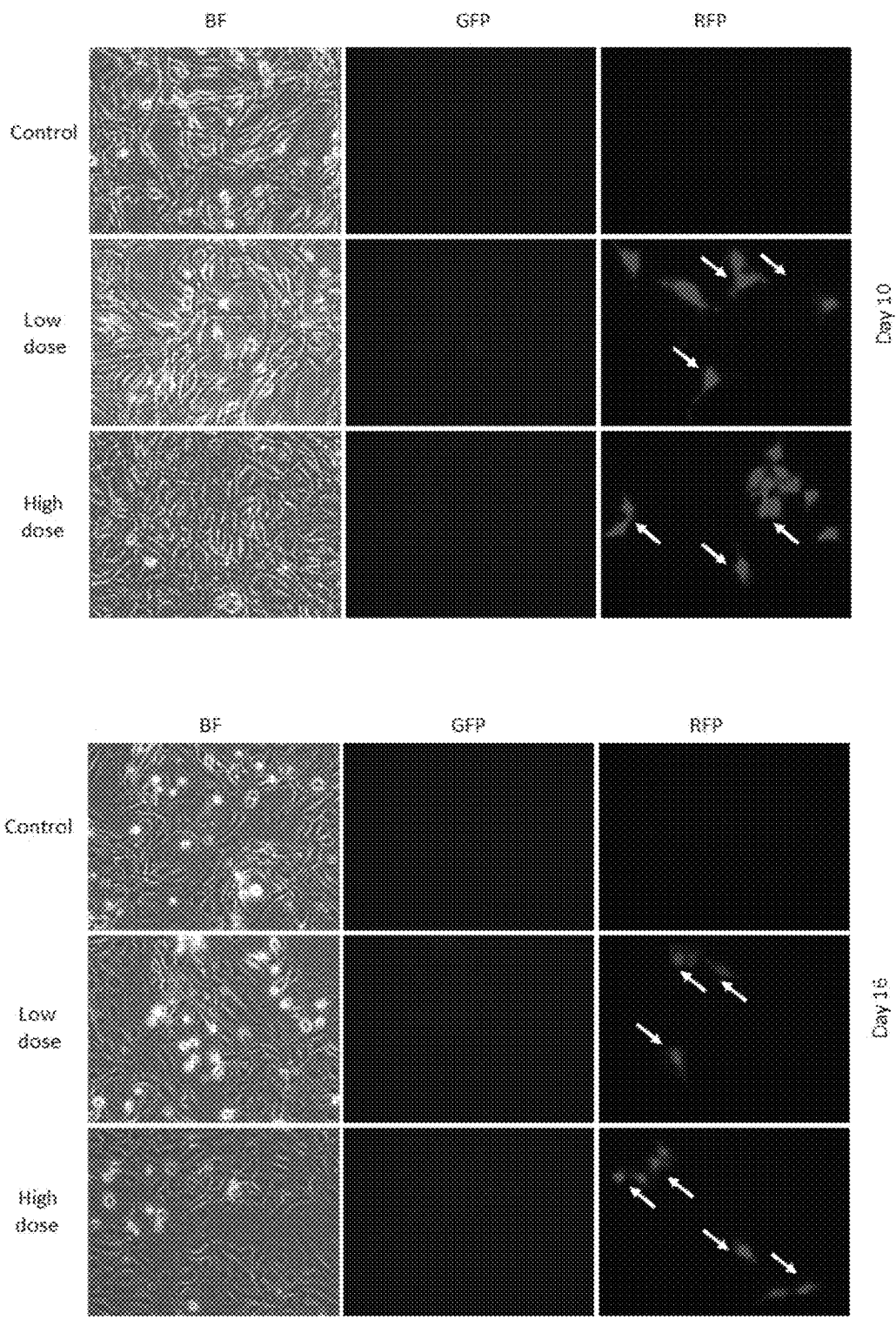
Figure 2C:
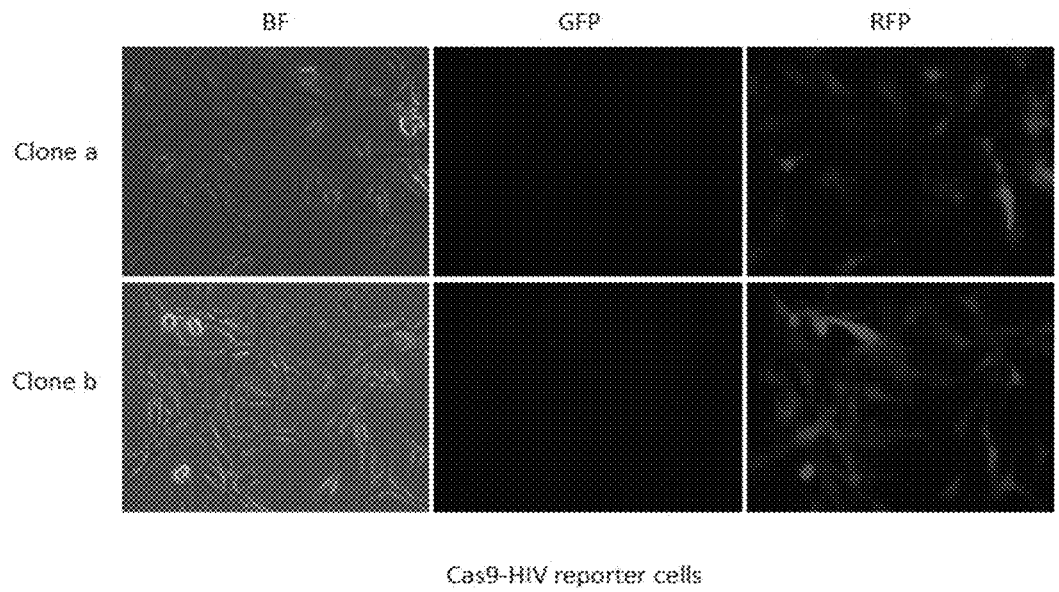

In one embodiment, a dual fluorescence HIV reporter red-green HIV (RGH) was used to establish a latent astrocyte cell model in which the cell HIV infection status can be easily monitored by fluorescence microscopy (FIGS. 2B-2C). According to this embodiment, only red fluorescence protein expression indicates HIV latent infection of the cells.

Using the fluorescence marker protein avoids a latent cell model using lentivirus titration and p24 measurement protocol. Moreover, the introduction of a fluorescence reporter establishes a marker for provirus status. Multiplex gRNAs are designed in such a way that a successful gRNA combination that targets and removes a segment of HIV provirus will delete the coding sequence of the fluorescence protein. Removal of coding sequence causes a loss of fluorescence from the "cured" cell, i.e., a cell from which HIV provirus is removed (FIG. 3A).

Figure 3A:
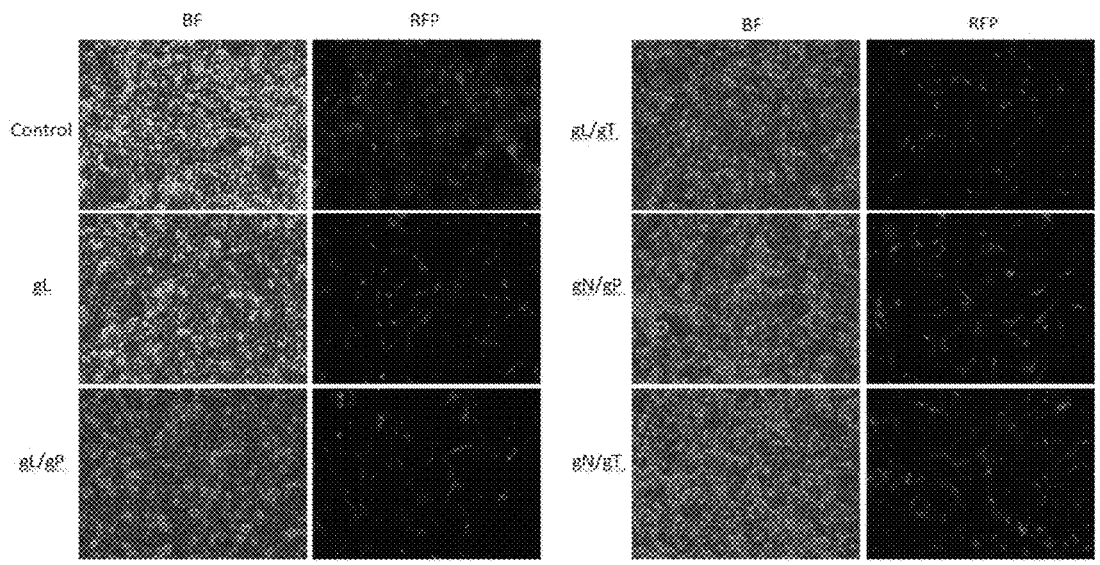
FIGS. 3A-3D. Screen and test of gRNAs targeting HIV provirus in latent Cas9 astrocyte cell clone. 3A. Test of gRNAs targeting HIV provirus in latent astrocyte cell clone. The selected astrocyte clone was treated with different gRNAs which target different regions of HIV provirus. Successful targeting results in the disappearance of red fluorescence protein expression. 3B. Quantitative stability of the gRNAs screen and test: The microplate of the treated clones was read by conventional plate reader at RFP channel. The red fluorescence protein expression levels were normalized by the protein level of the control group. Control group was presented as 100%. The 4-day time course readings indicated the repeatability and stability of the screening platform. 3C. Comparison of deletion efficiency of different targeting gRNAs: The microplates of different gRNA treated clones were read by conventional plate reader at RFP channel. Red fluorescence protein expression levels were normalized by the protein level of the control group. Control group was presented as 100%. The figure presented the data of four different experiments. The results are expressed by mean±SEM. They are compared with controls by on way ANOVA followed by Dunnett's multiple comparison test. Note: * means $p<0.05$;  means $p<0.01$; * means $p<0.001$. 3D. Confirmation of HIV provirus DNA deletion: I: gN/gP gRNA deletion. After gRNA treatment, DNA from cells was extracted. Specifically designed primers were used to detect HIV provirus DNA deletion. A band at specific size indicated the positive results of DNA deletion I: gN/gP gRNA deletion presents the HIV provirus DNA segment deletion with gN and gP; II: gN/gT gRNA deletion presents the HIV provirus DNA segment deletion with gN and gT. Two different clones were used in each experiment.

As such, all proposed deletions can be confirmed with genomic DNA PCR and fluorescence microscopy (FIG. 3A). A successful gRNA combination can be quantified by a decreased expression of fluorescence protein and the efficiency of the gRNAs corresponds to the extent of the decrease in fluorescence protein (FIG. 3C).

In one embodiment, the invention provides a method for screening candidate gRNAs to identify gRNAs that can be used for inactivation of latent HIV infection, for example, by disruption or removal of viral genome incorporated into the genome of a cell carrying the latent HIV infection. The gRNAs so identified can be used for treating, suppressing, and eradicating latent HIV infection in a subject.

As such, an embodiment of the invention provides a screening assay to identify one or more gRNAs from a plurality of gRNAs as effective or ineffective for removing or disrupting an HIV provirus genome integrated into the genome of a cell, wherein the screening assay comprises the steps of:

a) providing a cell or a culture of the cell having incorporated into the genome of the cell or cells: a gene that expresses a CRISPR-Cas protein and an HIV pseudovirus genome having a first marker gene encoding a first marker protein under the control of HIV-1 LTR promoter and a second marker gene encoding a second marker protein under the control of a constitutive promoter;

b) optionally, culturing the cell or the culture of the cell;

c) producing a plurality of test portions and a control portion of the culture provided in step a) or cultured in step b);

d) incubating each test portion from the plurality of test portions in the presence of one or more gRNAs from the plurality of gRNAs and incubating the control portion of the culture produced in step c), in the absence of gRNA from the plurality of gRNAs;

e) measuring the expression of the second marker protein in each of the plurality of test portions and/or the control portion after the incubation of step d); and f) identifying each gRNA from the plurality of gRNAs as:
  i) effective for removing or disrupting the HIV provirus genome integrated into the genome of the cell, if the expression of the second marker protein is lower in the test portion compared to the expression of the second marker protein in the control portion, or
  ii) ineffective for removing or disrupting the HIV provirus genome integrated into the genome of the cell, if the expression of the second marker protein is not lower in the test portion compared to the expression of the second marker protein in the control portion.

In one embodiment, a test portion is incubated with two or more candidate gRNAs to test whether a combination of gRNAs is effective or ineffective for removing or disrupting an HIV provirus genome integrated into the genome of the cell.

As such, the assay of the invention can identify one or more gRNAs from a library of gRNAs as effective or ineffective for removing or disrupting an HIV provirus genome integrated into the genome of a cell. A gRNA identified according to the methods described herein as effective for removing or disrupting an HIV provirus genome integrated into the genome of a cell can be used for treating, suppressing, or managing a latent HIV infection in a subject.

Various aspects described above in connection with type of cell, HIV pseudovirus genome, the CRISPR-Cas protein, the first and the second promoters, the first and the second marker proteins, etc., also apply to the screening assay described herein.

Certain embodiments of the invention provide kits containing HIV pseudovirus genome described herein, a polynucleotide containing a CRISPR-Cas gene (for example, Cas9 plasmid pX 459), one or more polynucleotides containing the first and the second genes with appropriate promoters (for example, the RGH plasmid), cells (with or without the HIV pseudovirus genome and/or a polynucleotide containing a CRISPR-Cas gene and/or the polynucleotides containing the first and/or the second genes as described herein), and reagents for carrying out the assays of the invention. Various aspects described above in connection with the assay methods and the type of cell, HIV pseudovirus genome, the CRISPR-Cas protein, the first and the second promoters, the first and the second marker proteins, etc., also apply to the kits described herein.

The screening method described herein provides a stable and reproducible approach to identifying HIV provirus gRNA targets (FIG. 2A). The PCR product examination, reduction of fluorescent protein reading, and fluorescent microscopy images are used to confirm the successful deletion of the DNA fragment of HIV provirus (FIG. 3A). The screening platform described herein can also be used for multiplex gRNA testing, for example, comparing efficiency of different gRNAs or combinations of gRNAs (FIG. 3C) because simultaneous application of two or more gRNAs can facilitate the deletion of critical segments of HIV provirus in cell latently infected with HIV. As such, the invention provides an accurate, simple, fast, and economical screening platform for identifying target gRNAs.

The established cell line provided herein can be used for mechanistic studies, such as HDAC2 gene knockout with gRNAs. The gRNAs selected based on the screening methods described herein can be tested in primary cells and in vivo studies.

Figure 4A:
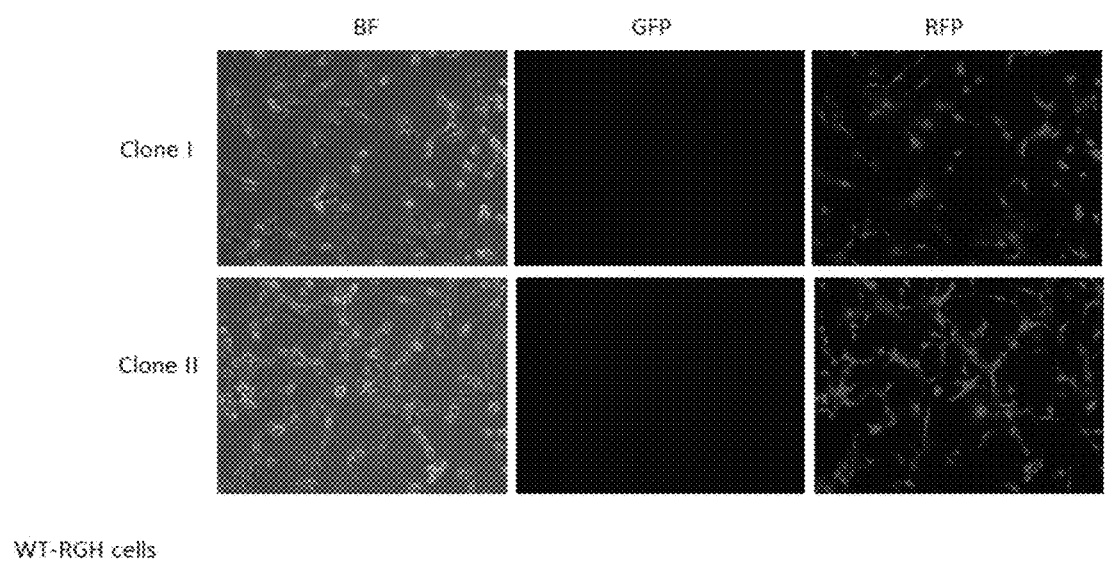
FIGS. 4A-4E. Cas9 and gRNAs targeting HIV provirus in latent astrocyte cell clone without Cas9 expression. 4A. Isolation of latent HIV astrocytes cell clones without Cas9 expression: Wild type astrocytes were infected with HIV reporter pseudo-type virus with VSVG. Latent HIV clones were isolated and examined by microscopy. 4B. Genomic integration of HIV reporter verification in cell clones: Multiple HIV reporter specific primers for different regions of constructs were used to verify the selected two positive clones that have the HIV reporter construct integrated in the genomes. Gapdh PCR products are used as a DNA extracts quality and loading control. Cas9 PCR was used to confirm the lack of Cas9 expression. 4C. Comparison of deletion efficiency of different targeting gRNAs: The microplates of different gRNA treated clones were read by conventional plate reader at RFP channel. The red fluorescence protein expression levels were normalized by the protein level of the control group. Control group was presented as 100%. The figure presented the data of four different experiments. The results are expressed by mean±SEM. They are compared with controls by on way ANOVA followed by Dunnett's multiple comparison test. Note: * means $p<0.05$;  means $p<0.01$; * means $p<0.001$. 4D. Confirmation of HIV provirus DNA deletion: I: gN/gP gRNA deletion. After gRNA treatment, DNA from the cells was extracted. 4E. Specifically designed primers were used to detect HIV provirus DNA deletion. A band at specific size indicated the positive results of DNA deletion. I: gN/gP gRNA deletion present the HIV provirus DNA segment deletion with gN and gP; II: gN/gT gRNA deletion presents the HIV provirus DNA segment deletion with gN and gT. Two different clones were used in each experiment.
Figure 4B:
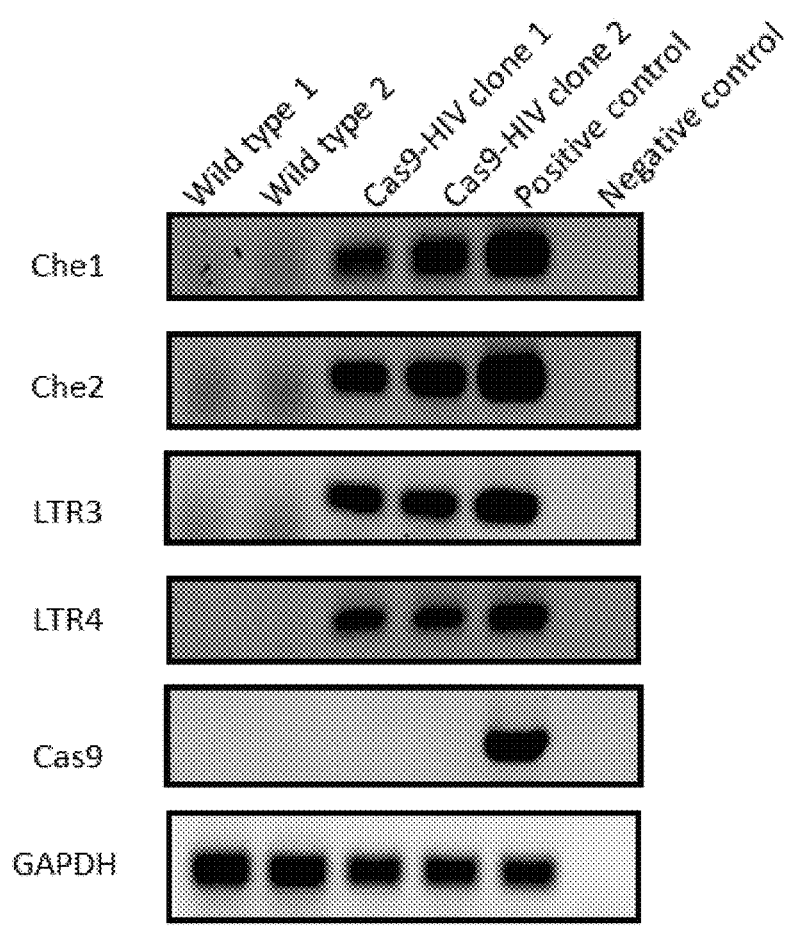
Figure 4C:
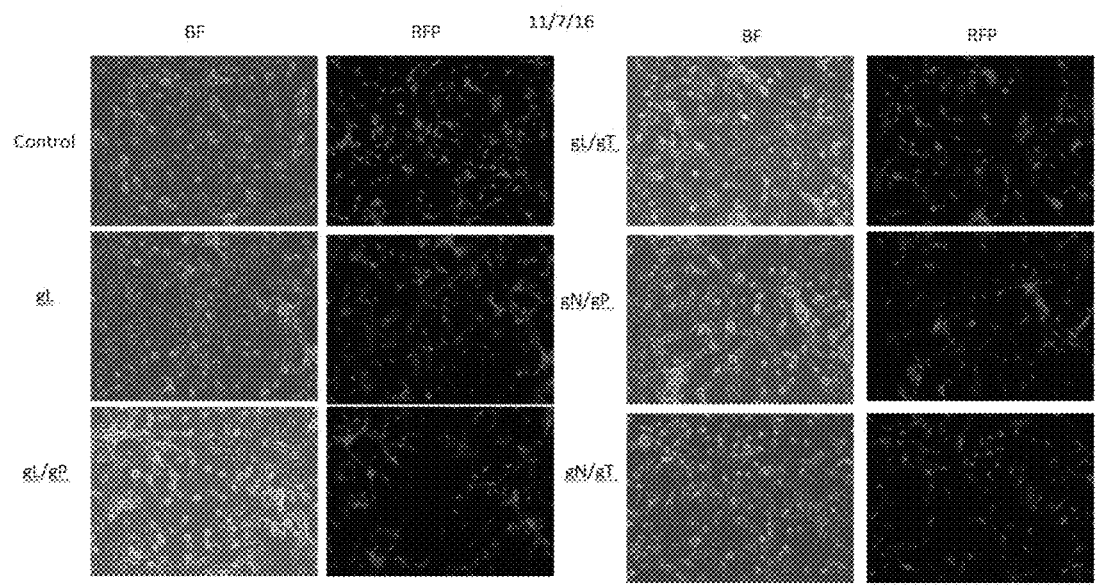
Figure 4D:
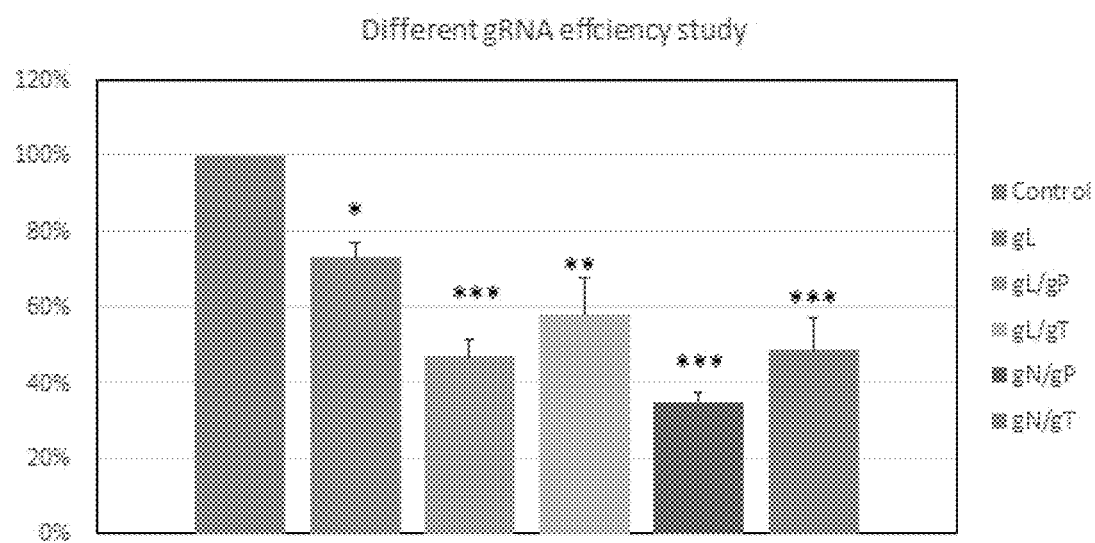
Figure 4E:
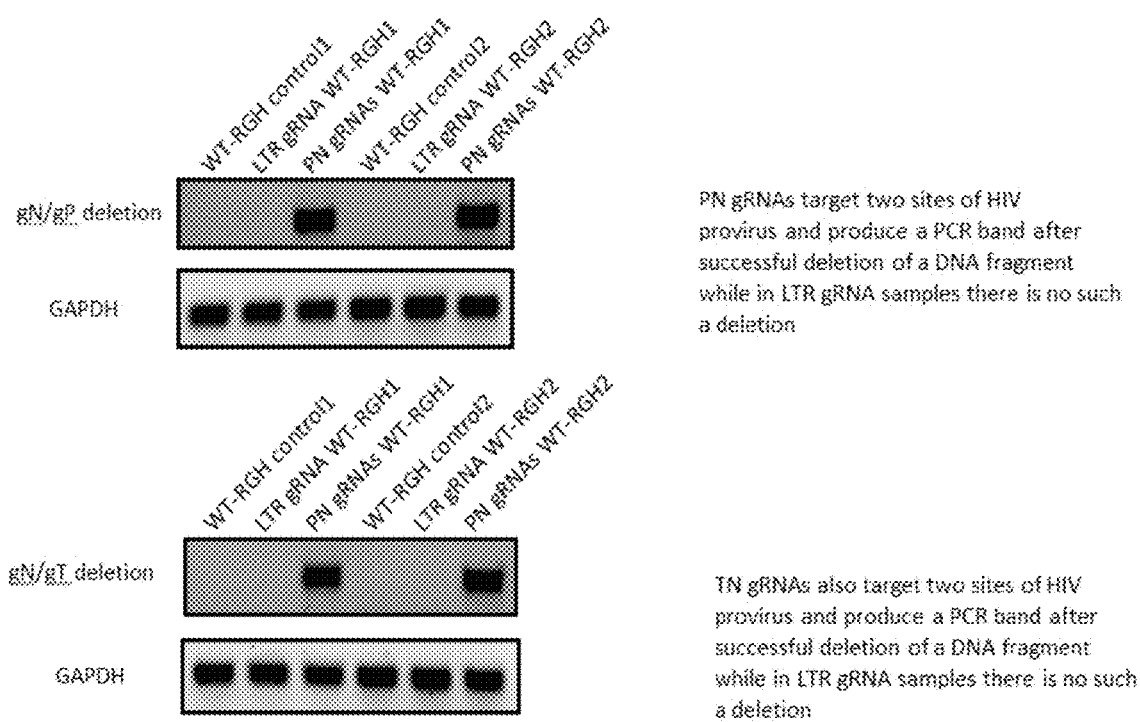

In one embodiment, the screened gRNAs are tested in RGH astrocytes, which don't express endogenous Cas9 (FIG. 4D). A composition comprising Cas9 protein and gRNA can be applied to RGH astrocytes (FIG. 4A). Introduction of the composition of Cas9 protein and an appropriate gRNA also causes disruption or removal of HIV pseudovirus integrated into the genome of a cell (FIG. 4E). These results are consistent with the results obtained with a cell having incorporated into the genome of the cell or cells: a gene that expresses a CRISPR-Cas protein and an HIV pseudovirus genome having a first marker gene encoding a first marker protein under the control of HIV-1 LTR promoter and a second marker gene inserted into the nef gene of the HIV pseudovirus and encoding a second marker protein under the control of a constitutive promoter, for example, RGH Cas9 astrocytes.

As such, the results of the screening method described herein can be translated into clinical use. Particularly, a gRNA identified according to the methods described herein in combination with CRISPR-Cas protein or a CRISPR-Cas plasmid can be delivered to a cell carrying a latent HIV infection to remove or disrupt the HIV provirus.

Accordingly, an embodiment of the invention provides a method for treating, suppressing, or eradicating a latent HIV infection in a subject. The method comprises administering into the cells of a subject that carry a latent HIV infection a composition comprising a CRISPR-Cas protein or CRISPR-Cas plasmid and gRNAs. Particular embodiments of the invention provide a method of treating, suppressing, or eradicating a latent HIV infection in a subject by administering a composition comprising Cas9 protein or Cas9 plasmid and a gRNAs into the cells of a subject that carry a latent HIV infection to remove or disrupt the HIV provirus, wherein the gRNA is selected from gLTR: CCGCCTAGCATTTCATCACG (SEQ ID NO: 13); gnef: CTGGCTAGAAGCACAAGAGG (SEQ ID NO: 14); gtat: ACCCACCTCCCAACCCCGAG (SEQ ID NO: 15); and gpol: CAGTACAATGTGCTTCCACA (SEQ ID NO: 16), or a combination of any two, three, or four gRNAs from gLTR, gnef, gtat and gpol. In certain embodiments, a combination of gnef and gtat or a combination of gnef and gpol is administered with Cas9 protein or Cas9 plasmid.

In one embodiment, the cell of a subject that carries a latent HIV infection is a brain cell, for example, astrocytes, microglia, and microphages in brain; a peripheral blood cell, for example, resting memory T cells and monocytes; or a lymphoid cell, for example, resting memory T cells.

In a particular embodiment, the cell of a subject that carries a latent HIV infection is a brain cell in the brain of a subject. For delivery of CRISPR-Cas protein or CRISPR-Cas plasmid and gRNAs into the brain, nanoparticle formulations that cross the blood brain barrier (BBB) can be used. In another embodiment, magnetic targeting is used to improve brain targeting and BBB transmigration of magnetic nanoparticle formulations.

Brain delivery using magnetic nanoparticles and magneto-electric nanoparticles is described by Ding et al. (2014), Jayant et al. (2015), Kaushik et al. (2016), Nair et al. (2013), and Sagar et al. (2015). These references are incorporated by reference in their entirety and using the nanoparticles described by these references is within the purview of the invention.

For example, magneto-electric nanoparticles have been used as carrier molecules that can cross the BBB and mediate controlled release of the loaded drugs. These nanoparticles cross the BBB using magnetic force induced on the nanoparticles by the magnetic field gradient.

In certain embodiments, the composition comprising a CRISPR-Cas protein or CRISPR-Cas plasmid and one or more gRNAs is specifically directed to one or more target cells. For example, a CRISPR-Cas protein or CRISPR-Cas plasmid and one or more gRNAs can be encapsulated in carriers, for example, liposomes, wherein the liposomes carry on their surface one or more binding agents that bind specifically molecules present on the surface of the target cells. The binding agents present on the surface of liposomes can be an aptamer, an antibody or an antigen binding fragment thereof, a ligand, etc. The binding agents that specifically recognize target cells through specific cell surface molecules can be used so that the CRISPR-Cas protein or CRISPR-Cas plasmid and one or more gRNAs can be specifically targeted and delivered to target cells (e.g., a cell carrying a latent HIV infection), without affecting the non-targeted cells (e.g., normal cells).

The compositions of the invention can be formulated using adjuvants, emulsifiers, pharmaceutically-acceptable carriers or excipients routinely provided in a pharmaceutical compositions. Optimum formulations can be designed by one of ordinary skill in the art and can include formulations for immediate release and/or for sustained release.

The compositions of the invention can be administered by any convenient route including subcutaneous, intradermal, intranasal, oral, intramuscular, intraperitoneal, or other parenteral or enteral route. A person of ordinary skill in the art can identify a particular route of administration suitable for a particular subject and a given bacterium and such embodiments are within the purview of the invention.

Material and Methods:

Establishment of Stable Cas9 Astrocytes with Integrated HIV Reporter

Astrocyte cell line U87 MG was purchased from ATCC, Manassas, Va. Cas9 vectors of pSpCas9 (BB)-2A-Puro (PX459) were purchased from Addgene, Cambridge, Mass. The vector linearization was done using BbsI (New England Biolabs, Ipswich, Mass.). Intact or linearized vectors were cleaned after the digestion and before transfection. Transfection was done by electroporation methods using BIO-RAD GenePulser Xcell system (BIORAD, Hercules, Calif.) and transfected cell clones were selected by puromycin resistance (Life technologies, Carlsbad, Calif.) at 0.31 µg/ml. The clones were first expanded and verified by PCR genotyping. Primers were as follows: CasF: GCTAGTCCGTTTTTAGCGCG (SEQ ID NO: 1); CasR1: AGAGTGAAGCAGAACGTGGG (SEQ ID NO: 2); Cas7F: ATGACCAGAAAGAGCGAGGA (SEQ ID NO: 3); and Cas7R, TTCCCTCGGTCACGTATTTC (SEQ ID NO: 4). The Cas9 protein expression in selected clones were confirmed by SDS-PAGE and western blot assay. One selected Cas9 clone were infected with HIV pseudo-virus consisting of an HIV fluorescence reporter RGH and VSVG. Several HIV reporter integrated Cas9 clones were selected and expanded. The integration of the HIV reporter was confirmed by genomic DNA PCR and red fluorescence protein expression. The PCR primers to check the integration of fluorescence HIV reporter are as follows: 1. mCherry region: CheF1: CACTACGACGCTGAGGTCAA (SEQ ID NO: 5); CheR1: CCAGGTCTCGAGCCTACTTG (SEQ ID NO: 6); CheF2: CCTGTCCCCTCAGTTCATGT (SEQ ID NO: 7); CheR2: CCCATGGTCTTCTTCTGCAT (SEQ ID NO: 8). 2. LTR region: LTRF1: ATCCACTGACCTTTGGATGG (SEQ ID NO: 9); LTRR1: GTACTCCGGATGCAGCTCTC (SEQ ID NO: 10); LTRF2: GGCTAATTCACTC-CCAACGA (SEQ ID NO: 11); and LTRR4: CTCAGGGT-CATCCATTCCAT (SEQ ID NO: 12). These clones are called HIV reporter Cas9 stable astrocytes.

Protein Samples Analysis by SDS-PAGE and Western Blot

The total protein of astrocytes was extracted with RIPA buffer and protease inhibitors cocktail from Fisher Scientific, Pittsburgh, Pa. After 4-15% gradient SDS-PAGE, the proteins were electro-transferred to Immobilon-P, PVDF membrane (Millipore Corp., Bedford, Mass.). Nonspecific protein binding sites on the membrane were blocked with nonfat dry milk. Primary monoclonal antibody of Cas9 from Fisher scientific and primary antibody of GAPDH from sigma, St. Louis, Mo. were used. After washing, the blots were incubated with the appropriate horseradish peroxidase-conjugated secondary antibody (Promega, Madison, Wis.). Blots were washed again and Supersignal West Pico chemiluminescence kit (Thermo Scientific, Waltham, Mass.) was used to detect target proteins. A BioRad ChemiDoc MP imaging system with Image Lab software was used to catch the images.

Cas9 Protein Localization by Immuno-Cyto-Fluorescence Experiment

Cells were cultured in the chamber slides (Thermo Scientific, Waltham, Mass.) until 60% confluency. Culture media was removed from the cells and cold PBS was used to wash the cells twice. The cells were fixed in 4% formaldehyde in PBS at 4° C. for 15 min, after which the cells was treated with 0.5% Triton X-100 in PBS. The fixed cells were washed with PBS and blocked with normal goat serum in PBS with Triton (PBST). The primary antibody incubation was usually 1 hr and cells were washed. The secondary antibody conjugated with Alexa488 was incubated with the cells for 1 hr and the cells were washed. The cells were counter stained with DAPI. Images were taken by a Zeiss Axio Observer fluorescence microscope (Carl Zeiss; Thornwood, N.Y., USA). Images were collected using ZEN2 2011 (blue edition) software (Carl Zeiss).

HIV RGH Reporter Pseudovirus Production and Infection

HEK293T cells were transfected with 10 µg RGH plasmid (NIH AIDS reagent program) and 15 µg VSVG plasmid (NIH AIDS reagent program) using lipofectamine 2000 (Invitrogen, Carlsbad, Calif.), incubated overnight, and fresh media were used to replace old media. After 24 to 48 hours incubation, cell culture supernatants containing pseudovirus were harvested and FBS was added a final concentration of 20% and the virus solution was filtered through a 0.45 µm pore size Millipore filter before storage at −80° C. Astrocyte lines were seeded at $10^5$ cell/well in a 6-well plate and incubated overnight. Next morning, fresh media was added to replace the old media and the cells were incubated for 2 to 3 hrs. A virus solution with polybrene at final concentration of 8 µg/ml was added to the cells. After further incubation of 24 to 48 hours, cells' infection statuses were examined under IX51 fluorescence microscope from Olympus (Olympus, Tokyo, Japan).

HIV Provirus Gene Targeting by CRISPR/Cas9 and gRNAs in Astrocytes

HIV provirus targeting sites for CRISPR/Cas9 system was designed by using bioinformatics software. The selected gRNA sequences are targeting LTR, nef, pol and tat gene regions. The sequences of the target regions are: gLTR: CCGCCTAGCATTTCATCACG (SEQ ID NO: 13); gnef: CTGGCTAGAAGCACAAGAGG (SEQ ID NO: 14); gtat: ACCCACCTCCCAACCCCGAG (SEQ ID NO: 15); and gpol: CAGTACAATGTGCTTCCACA (SEQ ID NO: 16). These gRNAs were used either alone or in combination of two (gLTR and gpol; gLTR and gtat; gnef and gpol; gnef and gtat) to transfect HIV reporter Cas9 stable cells. After 48 hours, the transfected cells and control cells were seeded into black 96 well plates to read the levels of red fluorescence protein expression by Biotek plate reader (Biotek, Winooski, Vt.). The background was subtracted from each read and fluorescent protein level of the control group was normalized as 100%. The deletion of HIV provirus with combination of gnef and gpol; gnef and gtat were examined by gnef and gpol deletion primers: DelPNF1: CTGGAT-GTGGGTGATGCATA (SEQ ID NO: 17); LTRR4, CTCA-GGGTCATCCATTCCAT (SEQ ID NO: 12); by gnef and gtat deletion primers: DelTNF1: GGCAAGTTTGTG-GAATTGGT (SEQ ID NO: 18); LTRR4, CTCAGGGT-CATCCATFCCAT (SEQ ID NO: 12).

Cas9 and gRNA Complex Treatment of Astrocytes Cas9 protein was diluted into a working Buffer (20 mM HEPES, 150 mM KCl, 5% Glycerol, 1 mM DTT, pH 7.5). RNA oligos (crRNA and tracrRNA) were dissolved in nuclease-Free TE Buffer, pH 7.4 and they were annealed in equimolar concentrations in a sterile microcentrifuge tube. Annealed RNA oligos and Cas9 proteins were incubated together to form a complex for 5 min. The complexes were mixed with lipofectamine RNAiMax (Thermo Scientific, Waltham, Mass.) according to manufacturers' guide. Then the complexes were added to the astrocytes for transfection for 48 hrs. Cells were examined for the CRISPR/Cas9 gene-editing efficiency by fluorescence measurement and genomic DNA PCR.

Statistics Processing

All the experiments were repeated three times or more. Fluorescence readings of 96 well plates were represented as mean±standard error of the mean (SEM). GraphPad Prism software was used to analyze the data using One-way analysis of variance to identify the significant differences between the groups. Dunnett's multiple comparison test was used as the post-test to compare the control group and each treatment group when there was a significant difference. The results were considered significant at p≤0.05.

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", include the phrases "consisting essentially of", "consists essentially of", "consisting", and "consists".

The phrases "consisting essentially of" or "consists essentially of" indicate that the claim encompasses embodiments containing the specified materials or steps and those that do not materially affect the basic and novel characteristic(s) of the claim.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional medium or agent is incompatible with the active agents described herein, its use in the compositions of the invention is contemplated.

When ranges are used herein, such as for dose ranges, combinations and subcombinations of ranges (e.g., subranges within the disclosed range), specific embodiments therein are intended to be explicitly included.

"Treatment" or "treating" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with the underlying disorder such that an improvement is observed in the patient, notwithstanding that the patient may still be afflicted with the underlying disease.

The term "effective amount" or "therapeutically effective amount" refers to that amount of active agents described herein that is sufficient to effect the intended application including but not limited to disease treatment. The therapeutically effective amount may vary depending upon the intended application and the subject and disease condition being treated, e.g., the weight and age of the subject, the severity of the disease condition, and the manner of administration. The term also applies to a dose that will induce a particular response in target cells, e.g., removal or disruption of an HIV provirus integrated into the genome of a cell. The specific dose will vary depending on the particular agents chosen, the dosing regimen to be followed, whether it is administered in combination with other compounds, timing of administration, the tissue to which it is administered, and the physical delivery system in which it is carried.

"Subject" refers to an animal, such as a mammal, for example a human.

As used herein "a cell that stably expresses a protein" has the gene encoding the protein incorporated into the genome of the cell. Therefore, the gene is transferred from generation to generation and the cell does not lose the ability to express the protein resulting from the loss of the gene.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1—Establishment of Stable Cas9 Expressing Astrocyte Cell Line

Figure 1B:
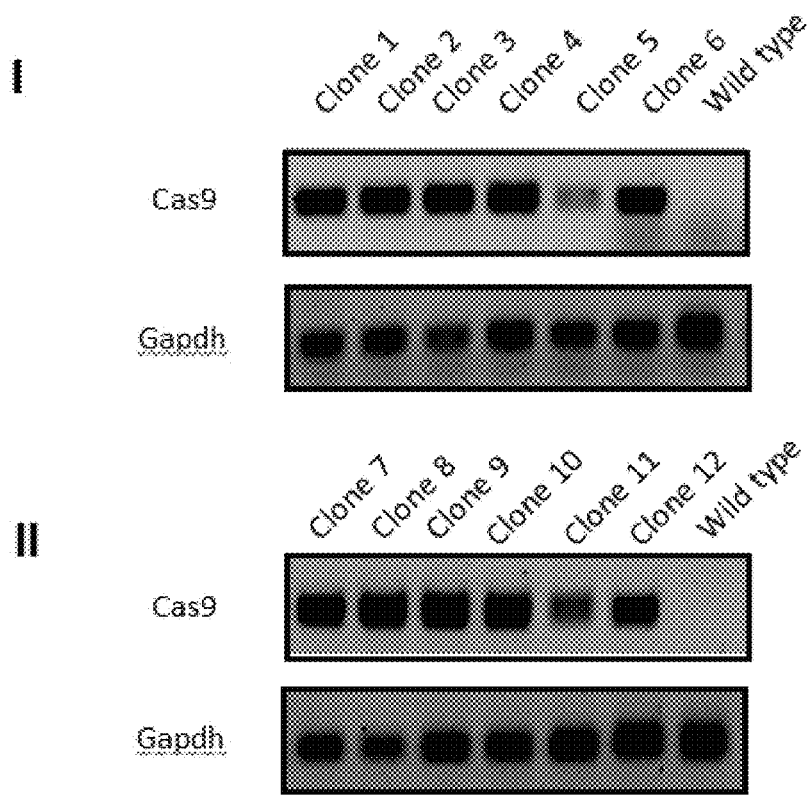
Figure 1C:
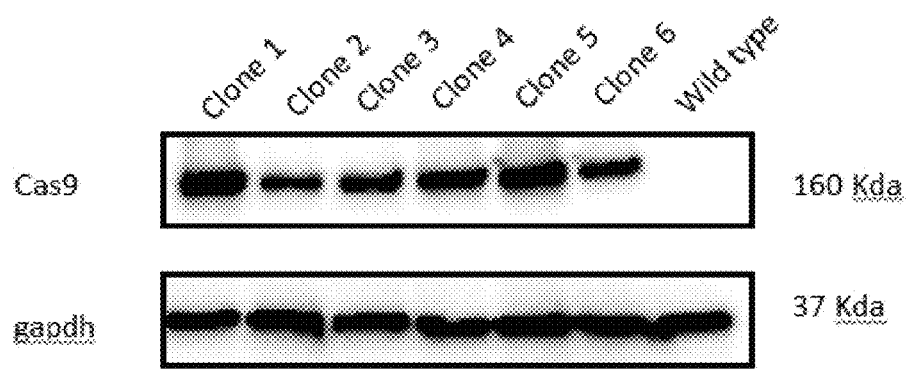
Figure 1D:
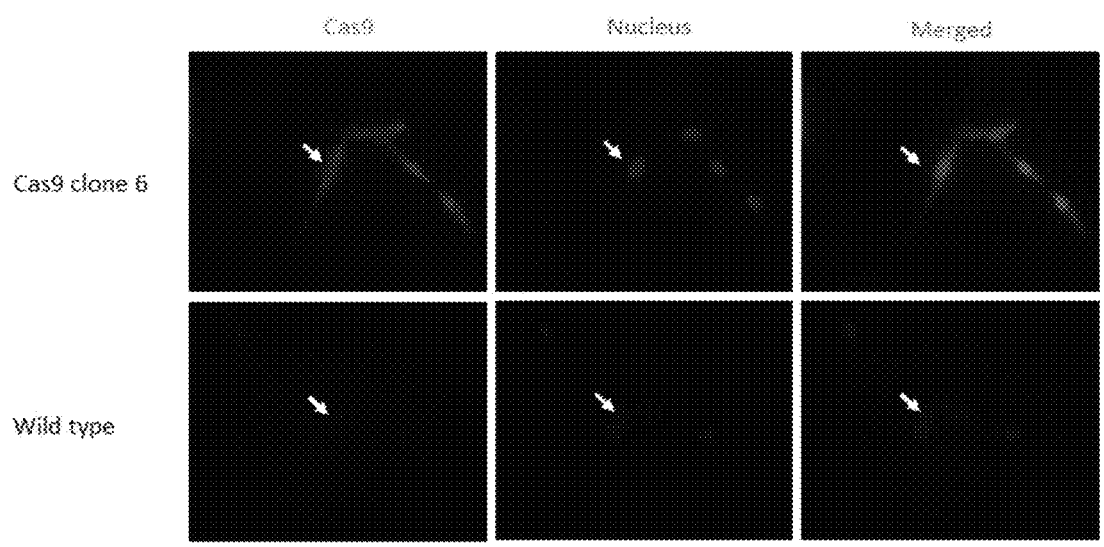

A genetically engineered astrocyte cell line stably expressing Cas9 was produced. An astrocyte cell line was transfected with intact or linearized Cas9 plasmid pX 459 and cell clones were selected for Cas9 plasmid integrated based on puromycin resistance. By testing the death curve of astrocyte under the puromycin resistance, the concentration of 0.31 µg/ml was chosen for selection. More positive cell clones were obtained from the linearized plasmid group compared to intact plasmid. The cell clones were expanded and genomic DNA was extracted for a PCR screen of Cas9 gene integration. Over ten cell clones provided a specific PCR product band, which was absent from the parent cell line (FIGS. 1B-1C). After the genomic DNA PCR screen, the protein extracts of positive cell clones were prepared for protein detection using SDS-PAGE and Western blot (FIG. 1C). The cell clones presented variable levels of Cas9 protein expression while wild type cell line had no expression of Cas9 protein. A clone (clone 6) with moderate Cas9 protein level was selected for further experiments (FIG. 1C). Because Cas9 protein has to enter the nucleus to perform its gene-editing function, intracellular localization of Cas9 protein in the cell clones was tested with immunocytochemistry to confirm the nuclear localization of Cas9 protein. Cas9 protein was localized in the nucleus according to the fluorescent nuclear stain (FIG. 2B).

EXAMPLE 2—Establishment of HIV Latent Astrocyte Cell Model with Stable Cas9 Expression To make a robust HIV latent cell model, a dual fluorescent protein HIV-reporter plasmid-RGH was used. The dual fluorescent protein HIV-reporter plasmid-RGH is described in the Dahabieh et al. (2013) reference, which is incorporated herein by reference in its entirety.

Figure 2D:
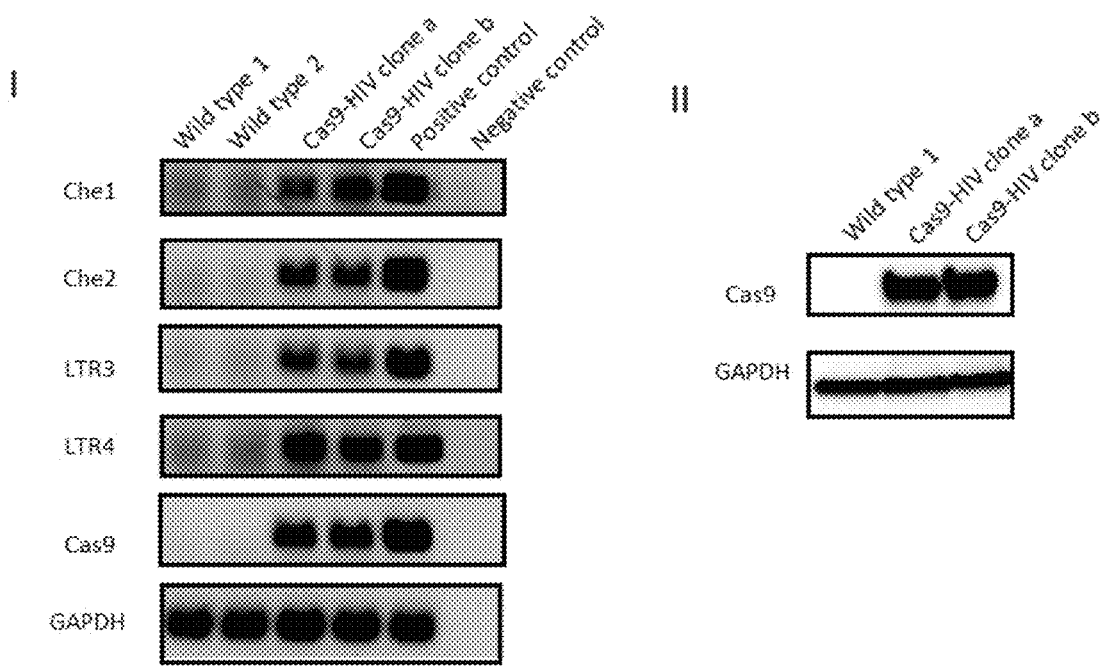

After RGH pseudovirus infection, when infected cells are in active state, green fluorescence proteins are expressed, and cells are green under fluorescent microscopy (FIG. 2B). When RGH pseudovirus infected cells are in latent stage, only red fluorescent proteins are expressed and cells are red under fluorescent microscopy. According to conventional method, astrocytes were infected with VSVG pseudo-type RGH HIV virus (as described in the Dahabieh et al. (2013) reference) and time-course study was performed of the cell infection status (FIG. 2B). Early during the infection, for example, over first few days, green fluorescent protein expression was observed, either alone or with red fluorescent protein (FIG. 2B); however, later in the infection, for example, ten days after infection, all the infected cells expressed red fluorescent protein only, which indicated the latent status of the infected cells (FIG. 2B). The infected that expressed red fluorescent protein after many passages are called RGH Cas9 astrocytes (FIG. 2B). Several RGH Cas9 clones were identified and their genomic DNA was extracted for verification. Several PCR primer pairs specific for different regions of HIV provirus were designed, including the mCherry coding region and LTR region. HIV provirus PCR products were detected in all the PCRs as indicated in FIG. 2D. These results confirmed genomic integration of RGH DNA into astrocytes genome. Also Cas9 PCR was performed to confirm that the cell line still contains in its genome Cas9 expression gene. Gapdh PCR was performed for DNA quality and loading control (FIG. 2D). Furthermore, the expression of the Cas9 protein was examined in the selected clones and Cas9 expression was observed (FIG. 1B).

EXAMPLE 3—Screening and Testing of gRNAs Targeting HIV Provirus in Latent Astrocyte Cell Lines An in vitro cell platform to screen gRNAs of CRISPR/Cas9 system for the removal of HIV provirus in HIV reporter Cas9 cells is provided. The specificity and gene-editing function of CRISPR/Cas9 system mainly depends on gRNAs. As an initial test, bioinformatics tools were applied to design several gRNAs targeting LTR region, pol gene region, tat gene region and nef gene region as indicated in FIG. 2A.

RGH Cas9 clones were transfected with those gRNAs either alone or in combination of two (gLTR and gpol; gLTR and gtat; gnef and gpol; gnef and gtat) to delete a DNA fragment which includes the mCherry coding region. Therefore a successful deletion should eliminate the expression of red fluorescent protein (FIG. 2A).

After transfection, those cells were first imaged with fluorescence microscopy as indicated in FIG. 3A. Reduced expression of red fluorescent protein was observed in gRNAs treated cells compared to control cells.

Figure 3B:
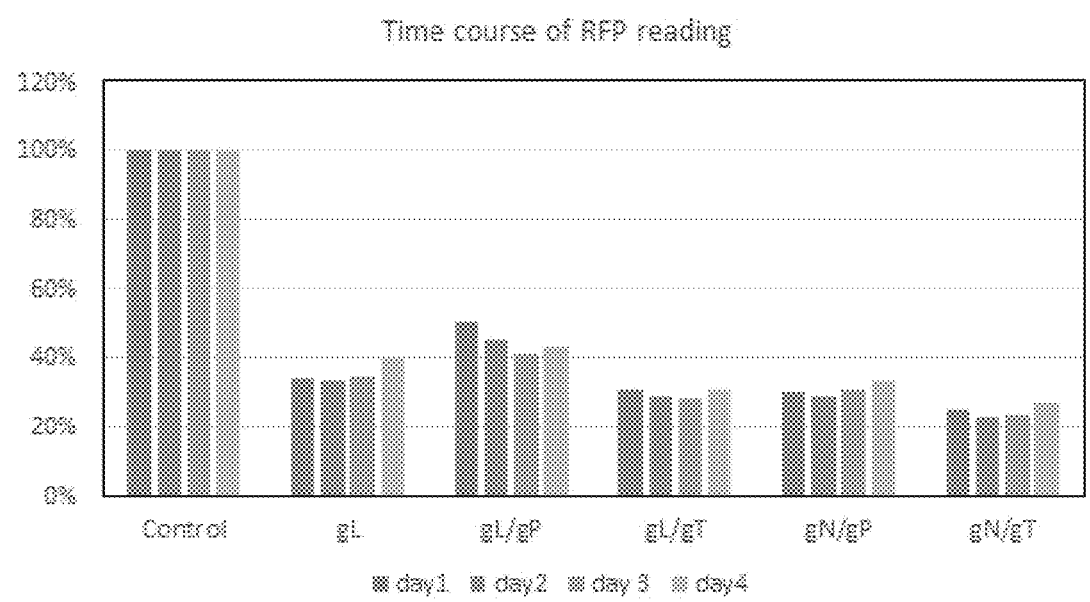
Figure 3C:
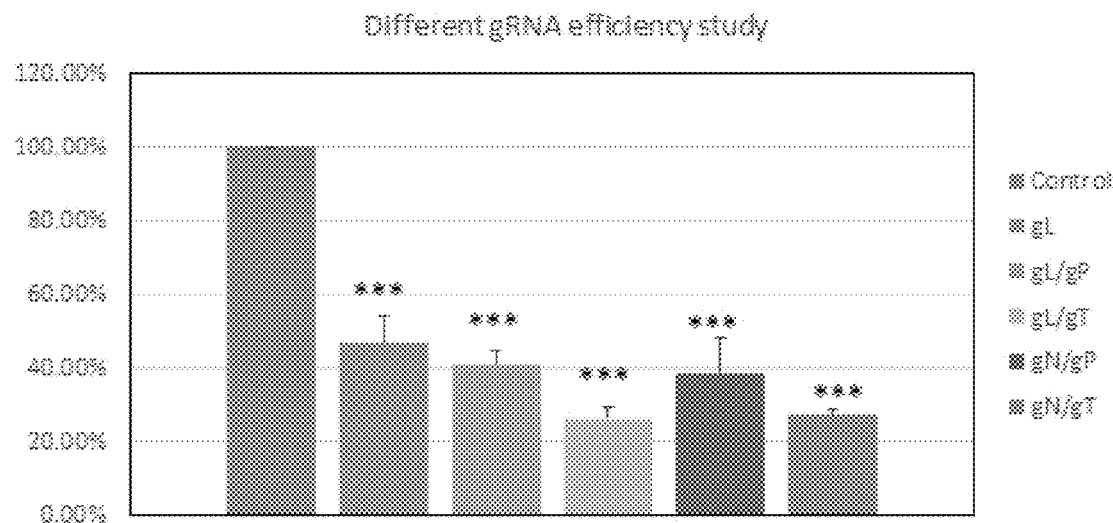

To quantify the fluorescence protein level decrease, the transfected cells were seeded to 96 well plates and a Biotek synergy HT plate reader was used for quantitative measurement of the cells' red fluorescent protein (FIG. 3B). The decrease in the red fluorescent protein reading is stable in a time course study when all samples are normalized to the control, which has 100% red fluorescence (FIG. 3B).

Significantly reduced expression of red fluorescent protein was observed in treated cells compared to control cells, which confirmed the fluorescence microscopy observation mentioned before (FIG. 3C). The order of the efficiency from high to low is LTR/tat, nef/tat, nef/pol, LTR/pol, LTR alone. In general, the efficiency of combination of LTR and other sites are marginally but not significantly better than that of LTR alone (FIG. 3C).

Figure 3D:
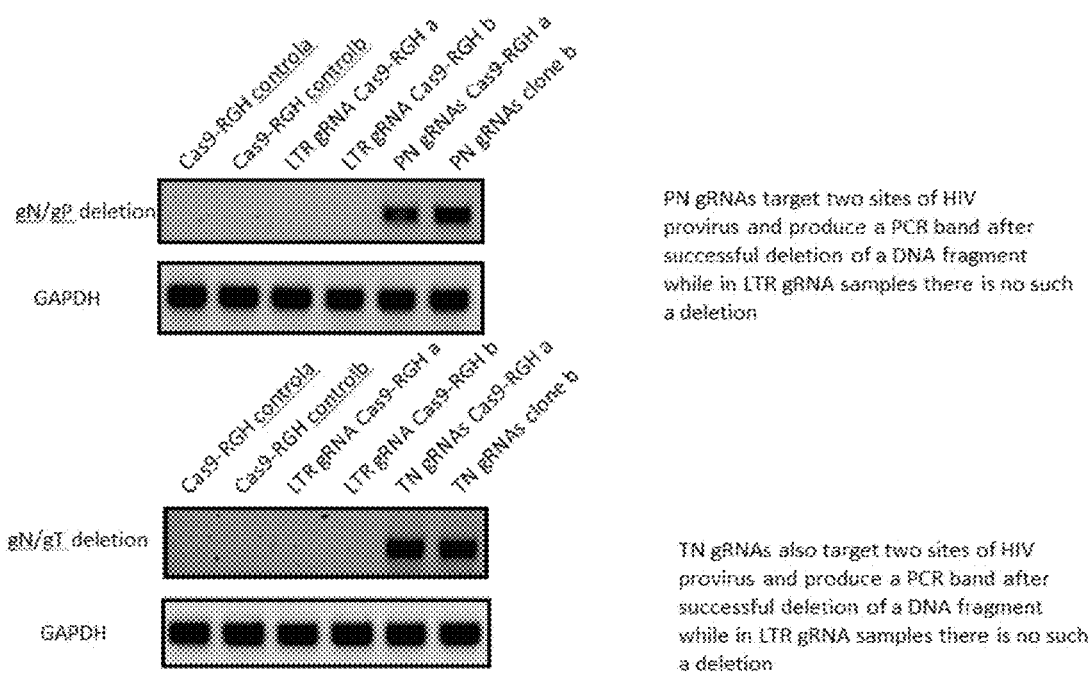

Genomic DNA was extracted from control and gRNA treated RGH Cas9 cells and the deletion of HIV provirus from host was examined using conventional PCR. The primer pairs were designed in such a way that only deleted genomic DNA could produce a band at a specific molecular size. Only two combinations produced feasible PCR products: gnef and gpol; and gnef and gtat. The upper panel of FIG. 3D shows the deletion from combination of gRNA targeting pol and nef; while the lower panel of FIG. 3D shows the deletion from combination of gRNA targeting tat and nef only. Each test in figure included samples from two different experiments.

Briefly, data from FIG. 3D confirmed the successful deletion of HIV provirus fragment using gRNAs. Furthermore, the deletion is specific because the LTR gRNA and control group did not produce such PCR products (FIG. 3D).

EXAMPLE 4—Cas9 and gRNA Complex Treatment of Astrocytes

Cells in an HIV patient do not express Cas9 protein. Therefore, to mimic real clinical situation, astrocyte clones were established with integrated HIV reporter. These cells were named RGH astrocytes (FIG. 4A).

Astrocyte genomic DNA was extracted and the integration of RGH HIV reporter was verified using multiple primer pairs that detect the coding sequence of mCherry and LTR (FIG. 4B). The specific PCR bands confirmed the integration of RGH HIV reporter. RGH HIV reporter was also confirmed using fluorescent microscopy (FIG. 4C).

Cas9 protein and gRNA complex were delivered to the RGH astrocytes. gRNAs are applied either alone or in combination of two (gLTR and gpol; gLTR and gtat; gnef and gpol; gnef and gtat) to delete a DNA fragment which includes the mCherry coding region. Therefore a successful deletion should eliminate the expression of red fluorescent protein.

The cells were imaged with fluorescence microscopy as indicated in FIG. 4C. Similar to the observations in RGH Cas9 astrocytes, reduced expression of red fluorescent protein was observed in the gRNAs treated cells compared to in control cells. The quantification of the fluorescence protein level confirmed a significant decrease as present in FIG. 4D.

To confirm the deletion of HIV provirus, genomic DNA was extracted from control and gRNA treated RGH cells and examined with specific primers to test the deletion resulted from gnef and gpol; gnef and gtat. As in RGH Cas9 cells, the successful deletion of HIV provirus was detected in RGH astrocytes. Each PCR test in FIG. 4B includes samples from two different experiments. FIG. 4D indicates successful deletion of HIV provirus fragment using gRNA combinations. Further, the deletion was specific because the LTR gRNA and control group did not produce such PCR products (FIG. 4E). These data confirm the biological function of the screened gRNAs.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

1. Chun T W, Carruth L, Finzi D, Shen X, DiGiuseppe J A, Taylor H, et al. Quantification of latent tissue reservoirs and total body viral load in HIV-1 infection. Nature. 1997; 387(6629):183-8.
2. Chun T W, Engel D, Mizell S B, Ehler L A, Fauci A S. Induction of HIV-1 replication in latently infected CD4+ T cells using a combination of cytokines. The Journal of experimental medicine. 1998; 188(1):83-91.
3. Finzi D, Hermankova M, Pierson T, Carruth L M, Buck C, Chaisson R E, et al. Identification of a reservoir for HIV-1 in patients on highly active antiretroviral therapy. Science (New York, N.Y.). 1997; 278(5341):1295-300.
4. Siliciano J D, Kajdas J, Finzi D, Quinn T C, Chadwick K, Margolick J B, et al. Long-term follow-up studies confirm the stability of the latent reservoir for HIV-1 in resting CD4+ T cells. Nature medicine. 2003; 9(6):727-8.
5. Chun T W, Engel D, Berrey M M, Shea T, Corey L, Fauci A S. Early establishment of a pool of latently infected, resting CD4(+) T cells during primary HIV-1 infection. Proceedings of the National Academy of Sciences of the United States of America. 1998; 95(15):8869-73.
6. Chavez L, Calvanese V, Verdin E. HIV Latency Is Established Directly and Early in Both Resting and Activated Primary CD4 T Cells. PLoS pathogens. 2015; 11(6):e1004955.
7. Bagasra O, Lavi E, Bobroski L, Khalili K, Pestaner J P, Tawadros R, et al. Cellular reservoirs of HIV-1 in the central nervous system of infected individuals: identification by the combination of in situ polymerase chain reaction and immunohistochemistry. AIDS (London, England). 1996; 10(6):573-85.

8. Fischer-Smith T, Croul S, Sverstiuk A E, Capini C, L'Heureux D, Regulier E G, et al. CNS invasion by CD14+/CD16+ peripheral blood-derived monocytes in HIV dementia: perivascular accumulation and reservoir of HIV infection. Journal of neurovirology. 2001; 7(6):528-41.
9. Petito C K, Chen H, Mastri A R, Torres-Munoz J, Roberts B, Wood C. HIV infection of choroid plexus in AIDS and asymptomatic HIV-infected patients suggests that the choroid plexus may be a reservoir of productive infection. Journal of neurovirology. 1999; 5(6):670-7.
10. McElrath M J, Steinman R M, Cohn Z A. Latent HIV-1 infection in enriched populations of blood monocytes and T cells from seropositive patients. The Journal of clinical investigation. 1991; 87(1):27-30.
11. Chun T W, Nickle D C, Justement J S, Meyers J H, Roby G, Hallahan C W, et al. Persistence of HIV in gut-associated lymphoid tissue despite long-term antiretroviral therapy. The Journal of infectious diseases. 2008; 197(5):714-20.
12. Smith P D, Meng G, Salazar-Gonzalez J F, Shaw G M. Macrophage HIV-1 infection and the gastrointestinal tract reservoir. Journal of leukocyte biology. 2003; 74(5):642-9.
13. Churchill M J, Gorry P R, Cowley D, Lal L, Sonza S, Purcell D F, et al. Use of laser capture microdissection to detect integrated HIV-1 DNA in macrophages and astrocytes from autopsy brain tissues. Journal of neurovirology. 2006; 12(2):146-52.
14. Churchill M J, Wesselingh S L, Cowley D, Pardo C A, McArthur J C, Brew B J, et al. Extensive astrocyte infection is prominent in human immunodeficiency virus-associated dementia. Annals of neurology. 2009; 66(2):253-8.
15. Narasipura S D, Kim S, Al-Harthi L. Epigenetic regulation of HIV-1 latency in astrocytes. Journal of virology. 2014; 88(5):3031-8.
16. Nath A. Eradication of human immunodeficiency virus from brain reservoirs. Journal of neurovirology. 2015; 21(3):227-34.
17. Chun T W, Stuyver L, Mizell S B, Ehler L A, Mican J A, Baseler M, et al. Presence of an inducible HIV-1 latent reservoir during highly active antiretroviral therapy. Proceedings of the National Academy of Sciences of the United States of America. 1997; 94(24):13193-7.
18. Brady T, Agosto I L M, Malani N, Berry C C, O'Doherty U, Bushman F. HIV integration site distributions in resting and activated CD4+ T cells infected in culture. AIDS (London, England). 2009; 23(12):1461-71.
19. Schneider M, Tigges B, Meggendorfer M, Helfer M, Ziegenhain C, Brack-Werner R. A new model for post-integration latency in macroglial cells to study HIV-1 reservoirs of the brain. AIDS (London, England). 2015; 29(10):1147-59.
20. Sunshine S, Kirchner R, Amr S S, Mansur L, Shakhbatyan R, Kim M, et al. HIV Integration Site Analysis of Cellular Models of HIV Latency with a Probe-Enriched Next-Generation Sequencing Assay. Journal of virology. 2016; 90(9):4511-9.
21. De Luca M A, Lai F, Corrias F, Caboni P, Bimpisidis Z, Maccioni E, et al. Lactoferrin- and antitransferrin-modified liposomes for brain targeting of the NK3 receptor agonist senktide: preparation and in vivo evaluation. International journal of pharmaceutics. 2015; 479(1):129-37.
22. Gallastegui E, Millan-Zambrano G, Terme J M, Chavez S, Jordan A. Chromatin reassembly factors are involved in transcriptional interference promoting HIV latency. Journal of virology. 2011; 85(7):3187-202.
23. Barboric M, Nissen R M, Kanazawa S, Jabrane-Ferrat N, Peterlin B M. NF-kappaB binds P-TEFb to stimulate transcriptional elongation by RNA polymerase II. Molecular cell. 2001; 8(2):327-37.
24. Lenasi T, Contreras X, Peterlin B M. Transcriptional interference antagonizes proviral gene expression to promote HIV latency. Cell host & microbe. 2008; 4(2):123-33.
25. Huang J, Wang F, Argyris E, Chen K, Liang Z, Tian H, et al. Cellular microRNAs contribute to HIV-1 latency in resting primary CD4+T lymphocytes. Nature medicine. 2007; 13(10):1241-7.
26. Patel P, Ansari M Y, Bapat S, Thakar M, Gangakhedkar R, Jameel S. The microRNA miR-29a is associated with human immunodeficiency virus latency. Retrovirology. 2014; 11:108.
27. Ruelas D S, Chan J K, Oh E, Heidersbach A J, Hebbeler A M, Chavez L, et al. MicroRNA-155 Reinforces HIV Latency. The Journal of biological chemistry. 2015; 290 (22):13736-48.
28. Fletcher C V, Staskus K, Wietgrefe S W, Rothenberger M, Reilly C, Chipman J G, et al. Persistent HIV-1 replication is associated with lower antiretroviral drug concentrations in lymphatic tissues. Proceedings of the National Academy of Sciences of the United States of America. 2014; 111(6):2307-12.
29. Letendre S, Marquie-Beck J, Capparelli E, Best B, Clifford D, Collier A C, et al. Validation of the CNS Penetration-Effectiveness rank for quantifying antiretroviral penetration into the central nervous system. Archives of neurology. 2008; 65(1):65-70.
30. Solas C, Lafeuillade A, Halfon P, Chadapaud S, Hittinger G, Lacarelle B. Discrepancies between protease inhibitor concentrations and viral load in reservoirs and sanctuary sites in human immunodeficiency virus-infected patients. Antimicrobial agents and chemotherapy. 2003; 47(1):238-43.
31. Heaton R K, Clifford D B, Franklin D R, Jr., Woods S P, Ake C, Vaida F, et al. HIV-associated neurocognitive disorders persist in the era of potent antiretroviral therapy: CHARTER Study. Neurology. 2010; 75(23):2087-96.
32. Heaton R K, Franklin D R, Jr., Deutsch R, Letendre S, Ellis R J, Casaletto K, et al. Neurocognitive change in the era of HIV combination antiretroviral therapy: the longitudinal CHARTER study. Clinical infectious diseases: an official publication of the Infectious Diseases Society of America. 2015; 60(3):473-80.
33. Heaton R K, Franklin D R, Ellis R J, McCutchan J A, Letendre S L, Leblanc S, et al. HIV-associated neurocognitive disorders before and during the era of combination antiretroviral therapy: differences in rates, nature, and predictors. Journal of neurovirology. 2011; 17(1):3-16.
34. Cong L, Ran F A, Cox D, Lin S, Barretto R, Habib N, et al. Multiplex genome engineering using CRISPR/Cas systems. Science (New York, N.Y.). 2013; 339(6121):819-23.
35. Hsu P D, Lander E S, Zhang F. Development and applications of CRISPR-Cas9 for genome engineering. Cell. 2014; 157(6): 1262-78.
36. Anders C, Niewoehner O, Duerst A, Jinek M. Structural basis of PAM-dependent target DNA recognition by the Cas9 endonuclease. Nature. 2014; 513(7519):569-73.

37. Nishimasu H, Ran F A, Hsu P D, Konermann S, Shehata S I, Dohmae N, et al. Crystal structure of Cas9 in complex with guide RNA and target DNA. Cell. 2014; 156(5):935-49.
38. Ebina H, Misawa N, Kanemura Y, Koyanagi Y. Harnessing the CRISPR/Cas9 system to disrupt latent HIV-1 provirus. Scientific reports. 2013; 3:2510.
39. Hu W, Kaminski R, Yang F, Zhang Y, Cosentino L, Li F, et al. RNA-directed gene editing specifically eradicates latent and prevents new HIV-1 infection. Proceedings of the National Academy of Sciences of the United States of America. 2014; 111(31): 11461-6.
40. Kaminski R, Bella R, Yin C, Otte J, Ferrante P, Gendelman H E, et al. Excision of HIV-1 DNA by gene editing: a proof-of-concept in vivo study. Gene therapy. 2016.
41. Kaminski R, Chen Y, Fischer T, Tedaldi E, Napoli A, Zhang Y, et al. Elimination of HIV-1 Genomes from Human T-lymphoid Cells by CRISPR/Cas9 Gene Editing. Scientific reports. 2016; 6:22555.
42. Dampier W, Nonnemacher M R, Sullivan N T, Jacobson J M, Wigdahl B. HIV Excision Utilizing CRISPR/Cas9 Technology: Attacking the Proviral Quasispecies in Reservoirs to Achieve a Cure. MOJ immunology. 2014; 1(4).
43. Zhu W, Lei R, Le Duff Y, Li J, Guo F, Wainberg M A, et al. The CRISPR/Cas9 system inactivates latent HIV-1 proviral DNA. Retrovirology. 2015; 12:22.
44. Dahabieh M S, Ooms M, Simon V, Sadowski I. A doubly fluorescent HIV-1 reporter shows that the majority of integrated HIV-1 is latent shortly after infection. Journal of virology. 2013; 87(8):4716-27.
45. Li W, Xu H, Xiao T, Cong L, Love M I, Zhang F, et al. MAGeCK enables robust identification of essential genes from genome-scale CRISPR/Cas9 knockout screens. Genome biology. 2014; 15(12):554.
46. Shalem O, Sanjana N E, Hartenian E, Shi X, Scott D A, Mikkelsen T S, et al. Genome-scale CRISPR-Cas9 knockout screening in human cells. Science (New York, N.Y.). 2014; 343(6166):84-7.
47. Wang T, Wei J J, Sabatini D M, Lander E S. Genetic screens in human cells using the CRISPR-Cas9 system. Science (New York, N.Y.). 2014; 343(6166):80-4.
48. Wang T, Birsoy K, Hughes N W, Krupczak K M, Post Y, Wei J J, et al. Identification and characterization of essential genes in the human genome. Science (New York, N.Y.). 2015; 350(6264):1096-101.
49. Chen S, Sanjana N E, Zheng K, Shalem O, Lee K, Shi X, et al. Genome-wide CRISPR screen in a mouse model of tumor growth and metastasis. Cell. 2015; 160(6):1246-60.
50. Gilbert L A, Larson M H, Morsut L, Liu Z, Brar G A, Torres S E, et al. CRISPR-mediated modular RNA-guided regulation of transcription in eukaryotes. Cell. 2013; 154(2):442-51.
51. Qi L S, Larson M H, Gilbert L A, Doudna J A, Weissman J S, Arkin A P, et al. Repurposing CRISPR as an RNA-guided platform for sequence-specific control of gene expression. Cell. 2013; 152(5):1173-83.
52. Gilbert L A, Horlbeck M A, Adamson B, Villalta J E, Chen Y, Whitehead E H, et al. Genome-Scale CRISPR-Mediated Control of Gene Repression and Activation. Cell. 2014; 159(3):647-61.
53. Horlbeck M A, Gilbert L A, Villalta J E, Adamson B, Pak R A, Chen Y, et al. Compact and highly active next-generation libraries for CRISPR-mediated gene repression and activation. eLife. 2016; 5.
54. Konermann S, Brigham M D, Trevino A E, Joung J, Abudayyeh O O, Barcena C, et al. Genome-scale transcriptional activation by an engineered CRISPR-Cas9 complex. Nature. 2015; 517(7536):583-8.
55. Ding H, Sagar V, Agudelo M, Pilakka-Kanthikeel S, Atluri V S, Raymond A, et al. Enhanced blood-brain barrier transmigration using a novel transferrin embedded fluorescent magneto-liposome nanoformulation. Nanotechnology. 2014; 25(5):055101.
56. Jayant R D, Atluri V S, Agudelo M, Sagar V, Kaushik A, Nair M. Sustained-release nanoART formulation for the treatment of neuroAIDS. International journal of nanomedicine. 2015; 10:1077-93.
57. Kaushik A, Jayant R D, Nikkhah-Moshaie R, Bhardwaj V, Roy U, Huang Z, et al. Magnetically guided central nervous system delivery and toxicity evaluation of magneto-electric nanocarriers. Scientific reports. 2016; 6:25309.
58. Nair M, Guduru R, Liang P, Hong J, Sagar V, Khizroev S. Externally controlled on-demand release of anti-HIV drug using magneto-electric nanoparticles as carriers. Nature communications. 2013; 4:1707.
59. Sagar V, Pilakka-Kanthikeel S, Atluri V S, Ding H, Arias A Y, Jayant R D, et al. Therapeutical Neurotargeting via Magnetic Nanocarrier: Implications to Opiate-Induced Neuropathogenesis and NeuroAIDS. Journal of biomedical nanotechnology. 2015; 11(10): 1722-33.

We claim:

1. A composition comprising a CRISPR-Cas protein, one or more gRNAs that are effective for removing or disrupting an HIV provirus genome integrated into the genome of a cell, magnetic nanoparticles, and liposomes.

2. The composition of claim 1, wherein the one or more gRNAs are selected from gLTR having the sequence of SEQ ID NO: 13; gnef having the sequence of SEQ ID NO: 14; gtat having the sequence of SEQ ID NO: 15; and gpol having the sequence of SEQ ID NO: 16.

3. The composition of claim 2, wherein the one or more gRNAs comprise a combination of gnef and gtat or a combination of gnef and gpol.

4. The composition of claim 2, wherein the liposomes carry on their surface one or more binding agents that bind specifically to molecules present on the surface of a target cell.

5. The composition of claim 1, wherein the CRISPR-Cas protein is Cas9.

6. A composition comprising a CRISPR-Cas plasmid encoding a Cas9 protein, one or more gRNAs that are effective for removing or disrupting an HIV provirus genome integrated into the genome of a cell, magnetic nanoparticles, and liposomes.

7. The composition of claim 6, wherein the one or more gRNAs are selected from gLTR having the sequence of SEQ ID NO: 13; gnef having the sequence of SEQ ID NO: 14; gtat having the sequence of SEQ ID NO: 15; and gpol having the sequence of SEQ ID NO: 16.

8. The composition of claim 7, wherein the one or more gRNAs comprise a combination of gnef and gtat or a combination of gnef and gpol.

9. The composition of claim 6, wherein the liposomes carry on their surface one or more binding agents that bind specifically to molecules present on the surface of a target cell.

10. A kit comprising:
   a polynucleotide molecule comprising a HIV pseudovirus genome comprising a first marker gene operably linked to a HIV-1 LTR promoter and encoding a first marker protein and a second marker gene operably linked to a constitutive promoter and encoding a second marker protein, wherein the second promoter and marker gene are located in the nef gene of the HIV pseudovirus genome;
   a CRISPR-Cas protein;
   at least one polynucleotide molecule comprising one or more gRNAs;
   magnetic nanoparticles;
   liposomes;
   reagents for detecting the expression of the marker proteins; and optionally, a cell.

11. The kit of claim 10, wherein the CRISPR-Cas protein is a Cas9 protein.

12. The kit of claim 10, wherein the at least one polynucleotide molecule comprises one or more gRNAs selected from gLTR having the sequence of SEQ ID NO: 13; gnef having the sequence of SEQ ID NO: 14; gtat having the sequence of SEQ ID NO: 15; and gpol having the sequence of SEQ ID NO: 16, or a combination.

13. The kit of claim 12, wherein the at least one polynucleotide molecule comprises a combination of gRNA gnef and gRNA gtat or a combination of gRNA gnef and gRNA gpol.

14. The kit of claim 10, wherein the second promoter and marker gene are located in the pol gene of the HIV pseudovirus genome.

15. The kit of claim 10, wherein the second promoter and marker gene are located in the tat gene of the HIV pseudovirus genome.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial
<220> FEATURE:
<223> OTHER INFORMATION: CasF primer

<400> SEQUENCE: 1
gctagtccgt ttttagcgcg                                              20

<210> SEQ ID NO 2
<211> LENGTH: 20
<212> TYPE: DNA
<213> ORGANISM: Artificial
<220> FEATURE:
```

```
<223> OTHER INFORMATION: CasR1 primer

<400> SEQUENCE: 2
agagtgaagc agaacgtggg                                               20

<210> SEQ ID NO 3
<211> LENGTH: 20
<212> TYPE: DNA
<213> ORGANISM: Artificial
<220> FEATURE:
<223> OTHER INFORMATION: Cas7F primer

<400> SEQUENCE: 3
atgaccagaa agagcgagga                                               20

<210> SEQ ID NO 4
<211> LENGTH: 20
<212> TYPE: DNA
<213> ORGANISM: Artificial
<220> FEATURE:
<223> OTHER INFORMATION: Cas7R primer

<400> SEQUENCE: 4
ttccctcggt cacgtatttc                                               20

<210> SEQ ID NO 5
<211> LENGTH: 20
<212> TYPE: DNA
<213> ORGANISM: Artificial
<220> FEATURE:
<223> OTHER INFORMATION: CheF1 primer

<400> SEQUENCE: 5
cactacgacg ctgaggtcaa                                               20

<210> SEQ ID NO 6
<211> LENGTH: 20
<212> TYPE: DNA
<213> ORGANISM: Artificial
<220> FEATURE:
<223> OTHER INFORMATION: CheR1 primer

<400> SEQUENCE: 6
ccaggtctcg agcctacttg                                               20

<210> SEQ ID NO 7
<211> LENGTH: 20
<212> TYPE: DNA
<213> ORGANISM: Artificial
<220> FEATURE:
<223> OTHER INFORMATION: CheF2 primer

<400> SEQUENCE: 7
cctgtcccct cagttcatgt                                               20

<210> SEQ ID NO 8
<211> LENGTH: 20
<212> TYPE: DNA
<213> ORGANISM: Artificial
<220> FEATURE:
<223> OTHER INFORMATION: CheR2 primer

<400> SEQUENCE: 8
cccatggtct tcttctgcat                                               20
```

```
<210> SEQ ID NO 9
<211> LENGTH: 20
<212> TYPE: DNA
<213> ORGANISM: Artificial
<220> FEATURE:
<223> OTHER INFORMATION: LTRF1 primer

<400> SEQUENCE: 9
atccactgac ctttggatgg                                              20

<210> SEQ ID NO 10
<211> LENGTH: 20
<212> TYPE: DNA
<213> ORGANISM: Artificial
<220> FEATURE:
<223> OTHER INFORMATION: LTRR1 primer

<400> SEQUENCE: 10
gtactccgga tgcagctctc                                              20

<210> SEQ ID NO 11
<211> LENGTH: 20
<212> TYPE: DNA
<213> ORGANISM: Artificial
<220> FEATURE:
<223> OTHER INFORMATION: LTRF2 primer

<400> SEQUENCE: 11
ggctaattca ctcccaacga                                              20

<210> SEQ ID NO 12
<211> LENGTH: 20
<212> TYPE: DNA
<213> ORGANISM: Artificial
<220> FEATURE:
<223> OTHER INFORMATION: LTRR4 primer

<400> SEQUENCE: 12
ctcagggtca tccattccat                                              20

<210> SEQ ID NO 13
<211> LENGTH: 20
<212> TYPE: DNA
<213> ORGANISM: Artificial
<220> FEATURE:
<223> OTHER INFORMATION: a gLTR sequence

<400> SEQUENCE: 13
ccgcctagca tttcatcacg                                              20

<210> SEQ ID NO 14
<211> LENGTH: 20
<212> TYPE: DNA
<213> ORGANISM: Artificial
<220> FEATURE:
<223> OTHER INFORMATION: a gnef sequence

<400> SEQUENCE: 14
ctggctagaa gcacaagagg                                              20

<210> SEQ ID NO 15
<211> LENGTH: 20
<212> TYPE: DNA
<213> ORGANISM: Artificial
<220> FEATURE:
<223> OTHER INFORMATION: a gtat sequence
```

```
<400> SEQUENCE: 15
acccacctcc caaccccgag                                              20

<210> SEQ ID NO 16
<211> LENGTH: 20
<212> TYPE: DNA
<213> ORGANISM: Artificial
<220> FEATURE:
<223> OTHER INFORMATION: a gpol sequence

<400> SEQUENCE: 16
cagtacaatg tgcttccaca                                              20

<210> SEQ ID NO 17
<211> LENGTH: 20
<212> TYPE: DNA
<213> ORGANISM: Artificial
<220> FEATURE:
<223> OTHER INFORMATION: a forward primer for detecting deletion of gnef
      and gpol

<400> SEQUENCE: 17
ctggatgtgg gtgatgcata                                              20

<210> SEQ ID NO 18
<211> LENGTH: 20
<212> TYPE: DNA
<213> ORGANISM: Artificial
<220> FEATURE:
<223> OTHER INFORMATION: a forward primer for detecting deletion of gnef
      and gtat

<400> SEQUENCE: 18
ggcaagtttg tggaattggt                                              20
```